United States Patent
Shelton, IV et al.

(10) Patent No.: US 7,513,408 B2
(45) Date of Patent: *Apr. 7, 2009

(54) MULTIPLE FIRING STROKE SURGICAL INSTRUMENT INCORPORATING ELECTROACTIVE POLYMER ANTI-BACKUP MECHANISM

(75) Inventors: Frederick E. Shelton, IV, Hillsboro, OH (US); Kenneth S. Wales, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 81 days.

This patent is subject to a terminal disclaimer.

(21) Appl. No.: 11/181,046

(22) Filed: Jul. 14, 2005

(65) Prior Publication Data
US 2006/0060630 A1   Mar. 23, 2006

Related U.S. Application Data

(60) Provisional application No. 60/591,694, filed on Jul. 28, 2004.

(51) Int. Cl.
*A61B 17/39* (2006.01)

(52) U.S. Cl. ............... 227/175.2; 227/175.1; 227/175.4; 227/19; 606/219

(58) Field of Classification Search ... 227/175.1–175.4, 227/19, 182.1, 178.1; 606/219, 220, 142, 606/143, 50, 51, 205
See application file for complete search history.

(56) References Cited

U.S. PATENT DOCUMENTS

| | | | |
|---|---|---|---|
| 2,711,461 A * | 6/1955 | Happe | 200/522 |
| 5,031,814 A | 7/1991 | Tompkins et al. | |
| 5,071,052 A | 12/1991 | Rodak et al. | |
| 5,137,198 A | 8/1992 | Nobis et al. | |
| 5,171,249 A | 12/1992 | Stefanchik et al. | |
| 5,202,914 A | 4/1993 | Kim et al. | |
| 5,263,629 A | 11/1993 | Trumbull et al. | |

(Continued)

FOREIGN PATENT DOCUMENTS

EP   0741966   11/1996

(Continued)

OTHER PUBLICATIONS

"Guidelines for Hand and Power Tools" website http://www.osha.gov/doc/outreachtraining/htmfiles/tools.html, OSHA, May 1996, p. 3.*

(Continued)

*Primary Examiner*—Rinaldi I. Rada
*Assistant Examiner*—Michelle Lopez
(74) *Attorney, Agent, or Firm*—Dean Garner

(57) ABSTRACT

A surgical stapling and severing instrument particularly suited to endoscopic procedures incorporates a handle that produces separate closing and firing motions to actuate an end effector. In particular, the handle produces multiple firing strokes in order to reduce the required amount of force required to fire (i.e., staple and sever) the end effector. A firing member reciprocates within an elongate shaft to the end effector to transfer this firing motion. A retraction spring retracts the firing member after full firing. Between firing strokes as the firing trigger is released, an anti-backup mechanism activates an electrical actuator (e.g., elecroactive polymer actuator) that is physically grounded to the handle to bind the firing member preventing inadvertent retraction.

20 Claims, 14 Drawing Sheets

U.S. PATENT DOCUMENTS

| | | | |
|---|---|---|---|
| 5,290,240 A | 3/1994 | Horres, Jr. | |
| 5,372,124 A | 12/1994 | Takayama et al. | |
| 5,387,194 A | 2/1995 | Williams et al. | |
| 5,389,098 A | 2/1995 | Tsuruta et al. | |
| 5,397,046 A | 3/1995 | Savage et al. | |
| 5,397,324 A | 3/1995 | Carroll et al. | |
| 5,403,312 A * | 4/1995 | Yates et al. | 606/50 |
| 5,413,267 A | 5/1995 | Solyntjes et al. | |
| 5,413,268 A | 5/1995 | Green et al. | |
| 5,431,668 A | 7/1995 | Burbank, III et al. | |
| 5,441,193 A | 8/1995 | Gravener | |
| 5,445,304 A | 8/1995 | Plyley et al. | |
| 5,465,895 A | 11/1995 | Knodel et al. | |
| 5,484,095 A | 1/1996 | Green et al. | |
| 5,503,638 A | 4/1996 | Cooper et al. | |
| 5,535,937 A | 7/1996 | Boiarski et al. | |
| 5,542,594 A | 8/1996 | McKean et al. | |
| 5,549,628 A | 8/1996 | Cooper et al. | |
| 5,562,239 A | 10/1996 | Boiarski et al. | |
| 5,584,425 A | 12/1996 | Savage et al. | |
| 5,599,329 A | 2/1997 | Gabbay | |
| 5,601,582 A | 2/1997 | Shelton, IV et al. | |
| 5,609,285 A | 3/1997 | Grant | |
| 5,624,452 A | 4/1997 | Yates | |
| 5,634,584 A | 6/1997 | Okorocha et al. | |
| 5,635,721 A | 6/1997 | Bardi et al. | |
| 5,653,721 A | 8/1997 | Knodel et al. | |
| 5,661,887 A | 9/1997 | Byrne et al. | |
| 5,665,285 A | 9/1997 | Hattori et al. | |
| 5,667,517 A | 9/1997 | Hooven | |
| 5,669,918 A | 9/1997 | Balazs | |
| 5,673,840 A | 10/1997 | Schulze et al. | |
| 5,673,841 A | 10/1997 | Schulze et al. | |
| 5,680,983 A | 10/1997 | Phyley et al. | |
| 5,688,270 A * | 11/1997 | Yates et al. | 606/51 |
| 5,692,668 A | 12/1997 | Schulze et al. | |
| 5,693,042 A | 12/1997 | Boiarski et al. | |
| 5,702,409 A | 12/1997 | Rayburn et al. | |
| 5,709,334 A | 1/1998 | Sorrentino et al. | |
| 5,735,445 A | 4/1998 | Vidal et al. | |
| 5,769,892 A | 6/1998 | Kingwell | |
| 5,779,130 A | 7/1998 | Alesi et al. | |
| 5,797,537 A | 8/1998 | Oberlin et al. | |
| 5,810,855 A | 9/1998 | Rayburn et al. | |
| 5,826,776 A | 10/1998 | Schulze et al. | |
| 5,829,662 A | 11/1998 | Allen et al. | |
| 5,855,565 A | 1/1999 | Bar-Cohen et al. | |
| 5,865,361 A | 2/1999 | Milliman et al. | |
| 5,876,401 A * | 3/1999 | Schulze et al. | 606/51 |
| 5,901,895 A | 5/1999 | Heaton et al. | |
| 5,902,312 A | 5/1999 | Frater et al. | |
| 5,908,427 A | 6/1999 | McKean et al. | |
| 5,918,791 A | 7/1999 | Sorrentino et al. | |
| 5,959,852 A | 9/1999 | Deloy et al. | |
| 5,964,774 A | 10/1999 | McKean et al. | |
| 6,010,054 A | 1/2000 | Johnson et al. | |
| 6,032,849 A | 3/2000 | Mastri et al. | |
| 6,063,097 A | 5/2000 | Oi et al. | |
| 6,079,606 A | 6/2000 | Milliman et al. | |
| 6,109,500 A | 8/2000 | Alli et al. | |
| 6,202,914 B1 | 3/2001 | Geoste et al. | |
| 6,302,311 B1 | 10/2001 | Adams et al. | |
| 6,330,965 B1 | 12/2001 | Milliman et al. | |
| 6,503,257 B2 | 1/2003 | Grant et al. | |
| 6,503,259 B2 | 1/2003 | Huxel et al. | |
| 6,577,899 B2 | 6/2003 | Lebel et al. | |
| 6,586,859 B2 | 7/2003 | Kornbluh et al. | |
| 6,595,852 B2 | 7/2003 | Wang | |
| 6,652,521 B2 | 11/2003 | Schulze | |
| 6,656,193 B2 | 12/2003 | Grant et al. | |
| 6,667,825 B2 | 12/2003 | Lu et al. | |
| 6,669,073 B2 | 12/2003 | Milliman et al. | |
| 6,716,233 B1 * | 4/2004 | Whitman | 606/219 |
| 6,740,079 B1 | 5/2004 | Eggers et al. | |
| 6,786,382 B1 | 9/2004 | Hoffman | |
| 6,830,174 B2 | 12/2004 | Hillstead et al. | |
| 6,835,173 B2 | 12/2004 | Couvillon, Jr. | |
| 6,840,246 B2 | 1/2005 | Downing | |
| 6,905,057 B2 | 6/2005 | Swayze et al. | |
| 6,923,804 B2 | 8/2005 | Eggers et al. | |
| 6,959,852 B2 | 11/2005 | Shelton, IV et al. | |
| 6,964,363 B2 | 11/2005 | Wales et al. | |
| 6,969,395 B2 | 11/2005 | Eskuri | |
| 6,978,921 B2 | 12/2005 | Shelton, IV et al. | |
| 6,981,628 B2 | 1/2006 | Wales | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,044,352 B2 | 5/2006 | Shelton, IV et al. | |
| 7,055,731 B2 | 6/2006 | Shelton, IV et al. | |
| 7,063,699 B2 | 6/2006 | Hess et al. | |
| 7,074,217 B2 | 7/2006 | Strul et al. | |
| 7,083,075 B2 | 8/2006 | Swayze et al. | |
| 7,111,769 B2 | 9/2006 | Wales et al. | |
| 7,140,528 B2 | 11/2006 | Shelton, IV | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,208,005 B2 | 4/2007 | Frecker et al. | |
| 7,213,736 B2 | 5/2007 | Wales et al. | |
| 7,364,061 B2 | 4/2008 | Swayze et al. | |
| 7,367,485 B2 | 5/2008 | Shelton, IV et al. | |
| 7,380,696 B2 | 6/2008 | Shelton, IV et al. | |
| 7,404,509 B2 | 7/2008 | Ortiz et al. | |
| 7,407,074 B2 | 8/2008 | Ortiz et al. | |
| 7,407,077 B2 | 8/2008 | Ortiz et al. | |
| 7,410,086 B2 | 8/2008 | Ortiz et al. | |
| 2001/0029384 A1 | 10/2001 | Nicholas et al. | |
| 2002/0074005 A1 | 6/2002 | Hobb et al. | |
| 2002/0165541 A1 | 11/2002 | Whitman | |
| 2003/0065358 A1 * | 4/2003 | Frecker et al. | 606/205 |
| 2003/0069474 A1 | 4/2003 | Couvillion et al. | |
| 2003/0199870 A1 | 10/2003 | Truckal et al. | |
| 2003/0207606 A1 | 11/2003 | Ho | |
| 2003/0236531 A1 | 12/2003 | Couvillon, Jr. | |
| 2004/0002726 A1 | 1/2004 | Nunez et al. | |
| 2004/0097971 A1 | 5/2004 | Hughett | |
| 2004/0050971 A1 | 6/2004 | Liddicoat | |
| 2004/0149802 A1 | 8/2004 | Whitman | |
| 2004/0232195 A1 | 11/2004 | Shelton, IV et al. | |
| 2004/0232196 A1 | 11/2004 | Shelton et al. | |
| 2004/0232197 A1 | 11/2004 | Shelton et al. | |
| 2005/0006429 A1 | 1/2005 | Wales et al. | |
| 2005/0006431 A1 | 1/2005 | Shelton, IV et al. | |
| 2005/0006434 A1 | 1/2005 | Wales et al. | |
| 2005/0067457 A1 | 3/2005 | Shelton et al. | |
| 2005/0067458 A1 | 3/2005 | Swayze et al. | |
| 2005/0085693 A1 | 4/2005 | Belsen et al. | |
| 2005/0165415 A1 | 7/2005 | Wales | |
| 2005/0173490 A1 * | 8/2005 | Shelton | 227/175.2 |
| 2006/0016853 A1 | 1/2006 | Racenet | |
| 2006/0022014 A1 * | 2/2006 | Shelton et al. | 227/175.2 |
| 2006/0022015 A1 * | 2/2006 | Shelton et al. | 227/176.1 |
| 2006/0025809 A1 | 2/2006 | Shelton, IV | |
| 2006/0025810 A1 | 2/2006 | Shelton, IV | |
| 2006/0025811 A1 | 2/2006 | Shelton, IV | |
| 2006/0025812 A1 | 2/2006 | Shelton, IV | |
| 2006/0025813 A1 | 2/2006 | Shelton, IV et al. | |
| 2006/0025816 A1 | 2/2006 | Shelton, IV | |
| 2006/0025817 A1 | 2/2006 | Ortiz et al. | |
| 2006/0041273 A1 | 2/2006 | Ortiz et al. | |
| 2006/0047302 A1 | 3/2006 | Ortiz et al. | |
| 2006/0047303 A1 | 3/2006 | Ortiz et al. | |
| 2006/0047305 A1 | 3/2006 | Ortiz et al. | |

| | | | |
|---|---|---|---|
| 2006/0047306 | A1 | 3/2006 | Ortiz et al. |
| 2006/0047307 | A1 | 3/2006 | Ortiz et al. |
| 2006/0047308 | A1 | 3/2006 | Ortiz et al. |
| 2006/0060630 | A1 | 3/2006 | Shelton, IV et al. |
| 2006/0212069 | A1 | 9/2006 | Shelton, IV et al. |

FOREIGN PATENT DOCUMENTS

| | | |
|---|---|---|
| EP | 1323384 | 7/2003 |
| EP | 1621137 | 2/2006 |
| EP | 1621141 | 2/2006 |
| EP | 1621143 | 2/2006 |
| EP | 1621151 | 2/2006 |
| EP | 1693008 | 8/2006 |
| WO | WO 99/02090 | 1/1999 |
| WO | WO 00/78222 | 12/2000 |
| WO | WO 01/62158 | 8/2001 |
| WO | WO 01/62163 | 8/2001 |
| WO | WO 03/088845 | 10/2003 |
| WO | WO 03/090630 | 11/2003 |
| WO | WO 03/094743 | 11/2003 |
| WO | WO 2004/014238 | 2/2004 |
| WO | WO 2004/050971 | 6/2004 |
| WO | WO 2004/086987 | 10/2004 |

OTHER PUBLICATIONS

EPO Search Report, Application No. 05254680.1, Jan. 12, 2006, pp. 1-5.
EPO Search Report, Application No. 05254694.2, Jan. 12, 2006, pp. 1-5.
EPO Search Report, Application No. 05254685.0, Jan. 12, 2006, pp. 1-5.
EPO Search Report, Application No. 05254695.9, Jan. 12, 2006, pp. 1-5.
EPO Search Report, Application No. 06255062.9, Nov. 23, 2006, pp. 1-3.
EPO Search Report, Application No. 06255053.8, Jan. 25, 2007, pp. 1-3.
EPO Search Report, Application No. 06255057.9, Jan. 29, 2007, pp. 1-3.
EPO Search Report, Application No. 06255058.7, Jan. 31, 2007, pp. 1-3.
EPO Search Report, Application No. 06255064.5, Feb. 9, 2007, pp. 1-3.
EPO Search Report, Application No. 06255065.2, Feb. 15, 2007, pp. 1-3.
U.S. Appl. No. 10/441,362, filed May 20, 2003, Ho.
U.S. Appl. No. 60/591,694, filed Jul. 28, 2004, Shelton, IV.
Non-Final Rejection dated Aug. 7, 2007 for U.S. Appl. No. 11/162,990.
Non-Final Rejection dated Aug. 29, 2007 for U.S. Appl. No. 11/181,046.
Non-Final Rejection dated Sep. 21, 2007 for U.S. Appl. No. 11/162,986.
Non-Final Rejection dated Sep. 21, 2007 for U.S. Appl. No. 11/162,988.
Notice of Allowance dated May 23, 2006 for U.S. Appl. No. 11/096,158.
Notice of Allowance dated Jul. 25, 2006 for U.S. Appl. No. 11/066,371.
Notice of Allowance dated Aug. 14, 2006 for U.S. Appl. No. 11/157,767.
Notice of Allowance dated Aug. 22, 2006 for U.S. Appl. No. 11/181,471.
Notice of Allowance dated Sep. 25, 2006 for U.S. Appl. No. 11/083,470.
Notice of Allowance dated Dec. 1, 2006 for U.S. Appl. No. 10/955,042.
Notice of Allowance dated Aug. 31, 2007 for U.S. Appl. No. 11/096,096.
Notice of Allowance dated Sep. 12, 2007 for U.S. Appl. No. 11/140,836.
Notice of Allowance dated Sep. 19, 2007 for U.S. Appl. No. 11/082,495.
Notice of Allowance dated Oct. 1, 2007 for U.S. Appl. No. 10/955,042.
Notice of Allowance dated Mar. 13, 2008 for U.S. Appl. No. 11/240,836.
Office Action dated Mar. 15, 2006 for U.S. Appl. No. 10/955,042.
Office Action dated Mar. 22, 2007 for U.S. Appl. No. 11/082,495.
Office Action dated Mar. 29, 2007 for U.S. Appl. No. 10/955,042.
Examination Report for Application 05254680, Sep. 22, 2006.
Examination Report for Application 05254685, Sep. 22, 2006.
Examination Report for Application 05254694, Sep. 22, 2006.
Examination Report for Application 05254695, Sep. 22, 2006.
U.S. Appl. No. 60/591,836, filed Jul. 28, 2004, Shelton, IV.
Final Rejection dated Oct. 18, 2006 for Application No. 11/096,096.
Non-Final Rejection dated Mar. 22, 2007 for Application No. 11/082,495.
Notice of Allowance dated Jan. 5, 2007 for Application No. 11/096,096.
Notice of Allowance dated Mar. 25, 2008 for Application No. 11/096,096.
Notice of Allowance dated Apr. 10, 2008 for Application No. 11/082,495.
Notice of Allowance dated Apr. 10, 2008 for Application No. 11/162,990.
Notice of Allowance dated Apr. 18, 2008 for Application No. 11/162,985.
Notice of Allowance dated Apr. 18, 2008 for Application No. 11/162,986.
Notice of Allowance dated Apr. 18, 2008 for Application No. 11/162,988.
Notice of Allowance dated Jun. 10, 2008 for Application No. 11/082,495.
Notice of Allowance dated Jun. 10, 2008 for Application No. 11/240,836.
Notice of Allowance dated Aug. 11, 2008 for Application No. 11/082,495.
EPO Search Report dated Feb. 29, 2008 for Application No. 05254681.9.
EPO Search Report dated Mar. 3, 2008 for Application No. 05254699.1.
EPO Search Report dated Feb. 26, 2008 for Application No. 05254700.7.
EPO Search Report dated Mar. 25, 2008 for Application No. 05254703.1.

* cited by examiner

MULTIPLE FIRING STROKE SURGICAL INSTRUMENT INCORPORATING ELECTROACTIVE POLYMER ANTI-BACKUP MECHANISM

CROSS REFERENCE TO RELATED APPLICATIONS

This application claims the benefit of U.S. provisional application Ser. No. 60/591,694, entitled "SURGICAL INSTRUMENT INCORPORATING AN ELECTRICALLY ACTUATED ARTICULATION MECHANISM" to Shelton IV, filed 28 Jul. 2004.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments that preclude inadvertent firing.

BACKGROUND OF THE INVENTION

Endoscopic and laparoscopic surgical instruments are often preferred over traditional open surgical devices since a smaller incision tends to reduce the post-operative recovery time and complications. The use of laparoscopic and endoscopic surgical procedures has been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

Significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Generally, a single closing stroke followed by a single firing stroke is a convenient and efficient way to perform severing and stapling. However, in some instances, multiple firing strokes are desirable. For example, surgeons select a length of staple cartridge for the desired length of the cut from a range of jaw sizes. Longer staple cartridges require a longer firing stroke. Thus, to effect the firing, a hand-squeezed trigger is required to exert a larger force for these longer staple cartridges in order to sever more tissue and drive more staples as compared to a shorter staple cartridge. It would be desirable for the amount of force to be lower and comparable to shorter cartridges so as not to exceed the hand strength of some surgeons. In addition, some surgeons, not familiar with the larger staple cartridges, may become concerned that binding or other malfunction may occur when an unexpectedly higher force is required.

In co-pending and commonly-owned U.S. Pat. Appl. Publ. 2005/0067457 A1, Ser. No. 10/673,929, "SURGICAL STAPLING INSTRUMENT WITH MULTISTROKE FIRING INCORPORATING AN ANTI-BACKUP MECHANISM" to Shelton et al. filed on Sep. 29, 2003, the disclosure of which is hereby incorporated by reference in its entirety, an advantageous anti-backup mechanism mechanically disengages as a firing member distally moves during each firing stroke and then engages as the firing trigger is released between firing strokes, preventing inadvertent retraction. Upon full firing travel, a mechanical linkage is tripped that disengages the anti-backup mechanism, allowing a retraction spring to retract the firing member. Thereby, the advantages of multiple firing strokes were realized in combination with automatic retraction.

More recently, a similar anti-backup mechanism is described in two U.S. patent application Ser. Nos. 11/052,387 entitled "SURGICAL STAPLING INSTRUMENT INCORPORATING A MULTI-STROKE FIRING MECHANISM WITH RETURN SPRING ROTARY MANUAL RETRACTION SYSTEM" to Shelton et al., and U.S. patent application Ser. No. 11/052,632 entitled "SURGICAL STAPLING INSTRUMENT INCORPORATING A FIRING MECHANISM HAVING A LINKED RACK TRANSMISSION" to Swayze et al., both filed on 8 Feb. 2005, the disclosure of both being hereby incorporated by reference in its entirety.

While these mechanically controlled anti-backup mechanisms provide significant clinical utility, it is desirable to provide an alternate approach to preventing inadvertent retraction that allows for additional functionality.

Consequently, a significant need exists for an improved surgical stapling and severing instrument that performs multistroke firing for increased firing travel and/or reduced force to fire with a reliable and configurable prevention of inadvertent firing retraction between strokes.

BRIEF SUMMARY OF THE INVENTION

The invention overcomes the above-noted and other deficiencies of the prior art by providing a surgical stapling and severing instrument that advantageously incorporates a multiple firing stroke handle that actuates a long end effector without undue manual force required by the surgeon. A retraction bias on firing components assists in retracting a firing mechanism after full firing travel. Advantageously, an electrical actuator assists in preventing inadvertent retraction of firing components between firing strokes.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
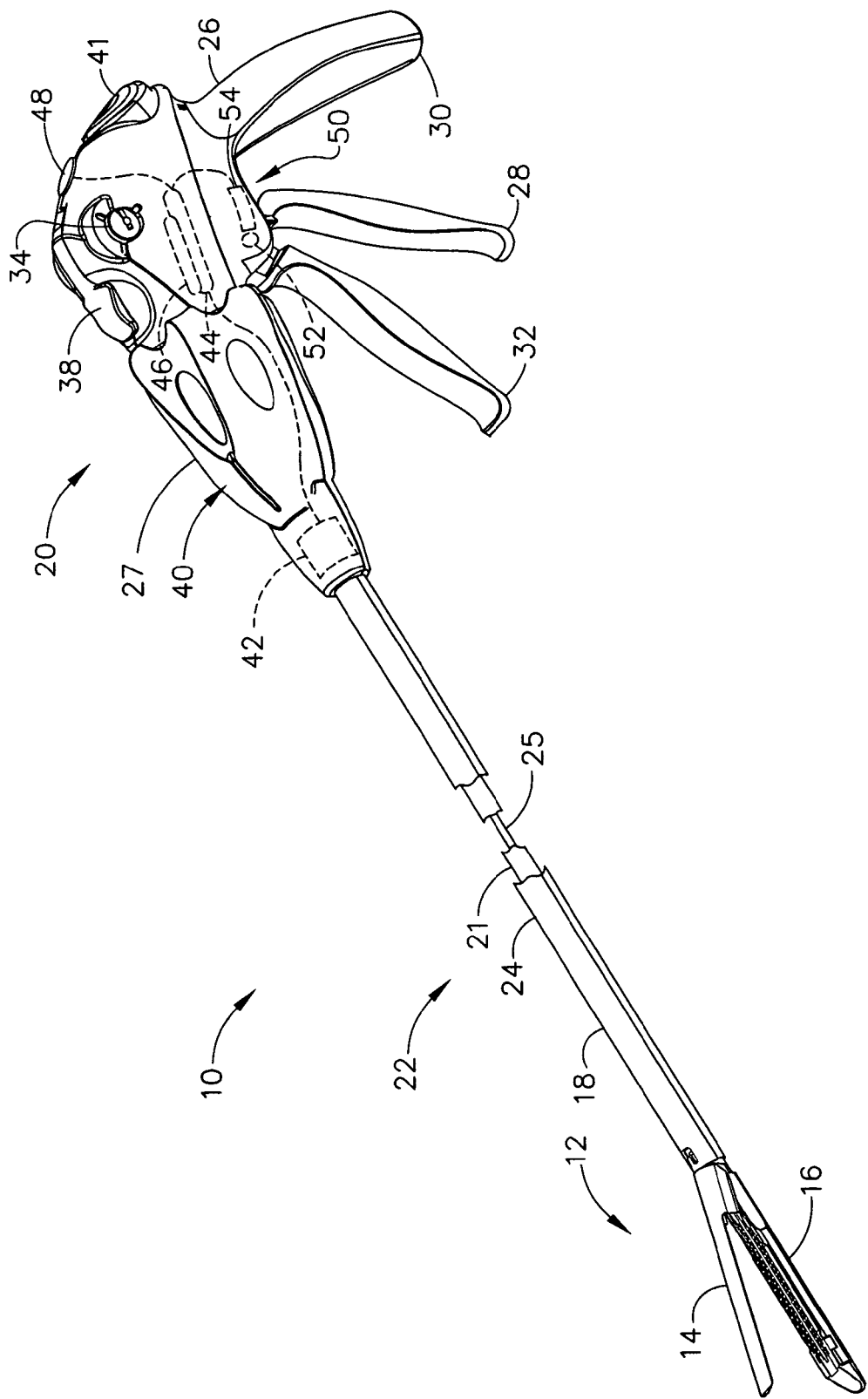
FIG. 1 is a left front perspective view of a surgical stapling and severing instrument incorporating a multistroke firing mechanism with an electrically actuated anti-backup mechanism in a handle portion and a partially cut-away elongate shaft.
Figure 2:
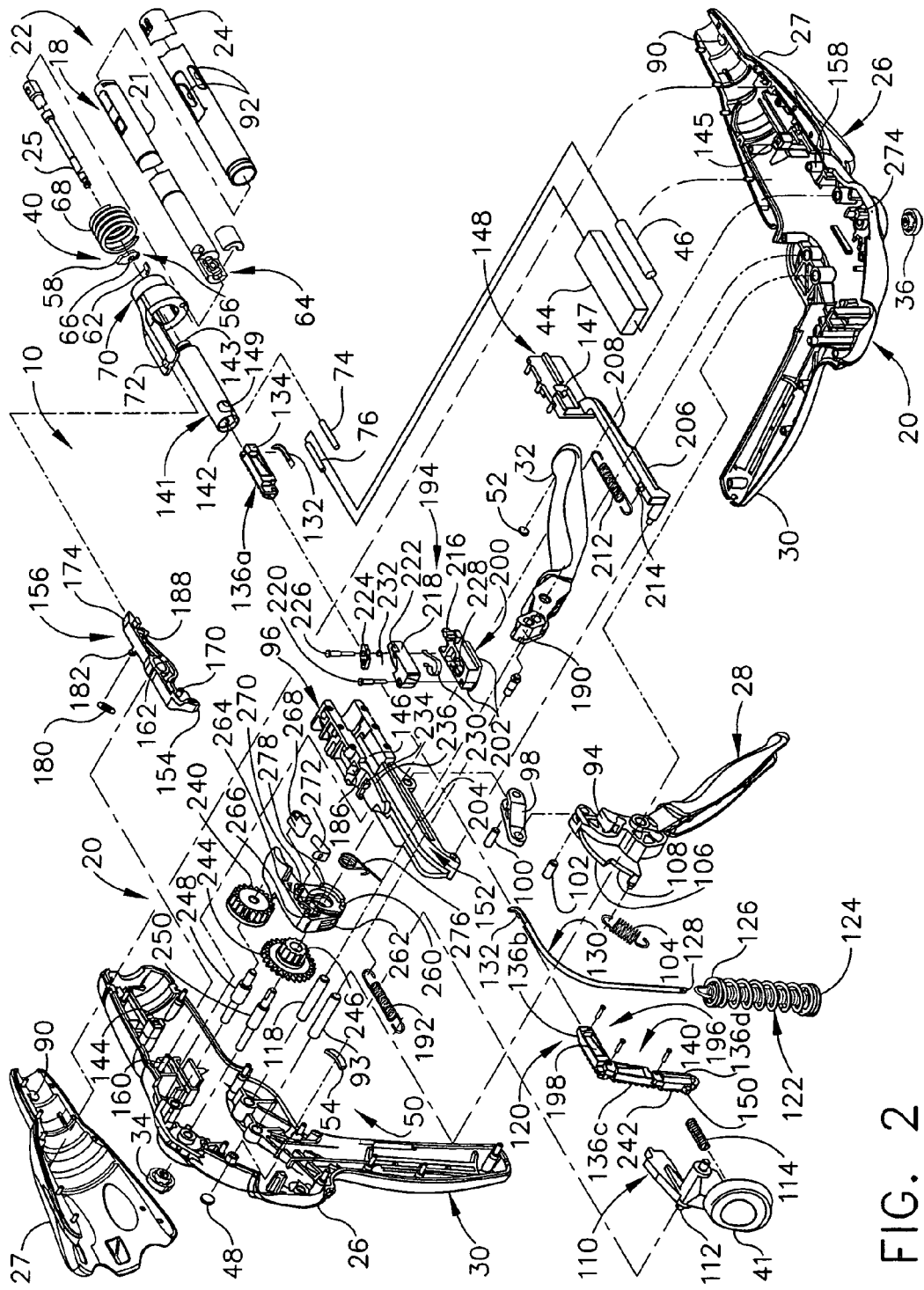
FIG. 2 is a right aft perspective disassembled view of the handle and an elongate shaft with an end effector omitted from the surgical stapling and severing instrument of FIG. 1 with one version of the electrically actuated anti-backup mechanism including a hybrid electroactive polymer (EAP)-mechanically actuated anti-backup locking plate.
Figure 3:
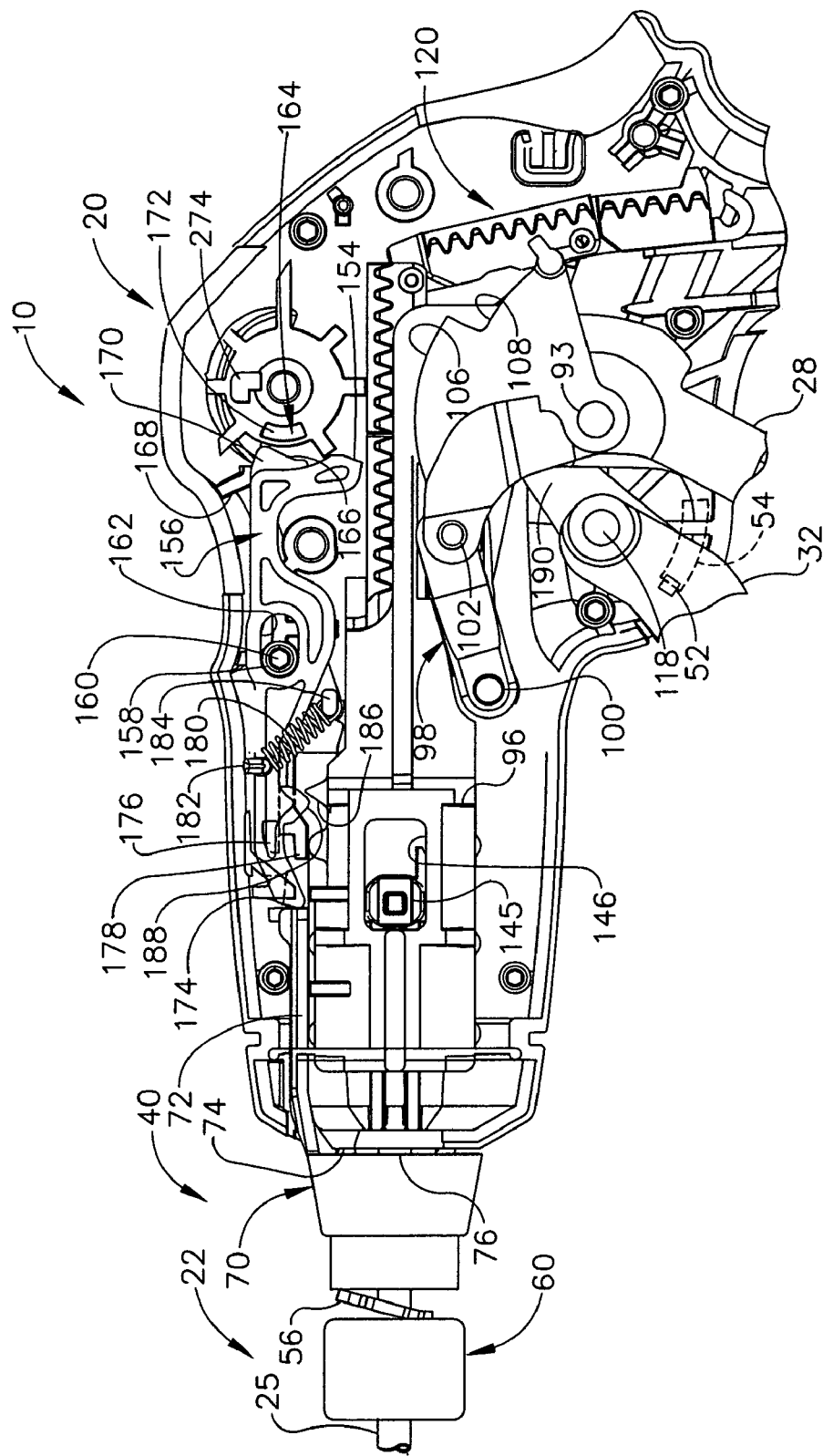
FIG. 3 is a right side view of an upper portion of the handle of FIG. 2 with the right housing half shell and rotation knob removed.
Figure 3A:
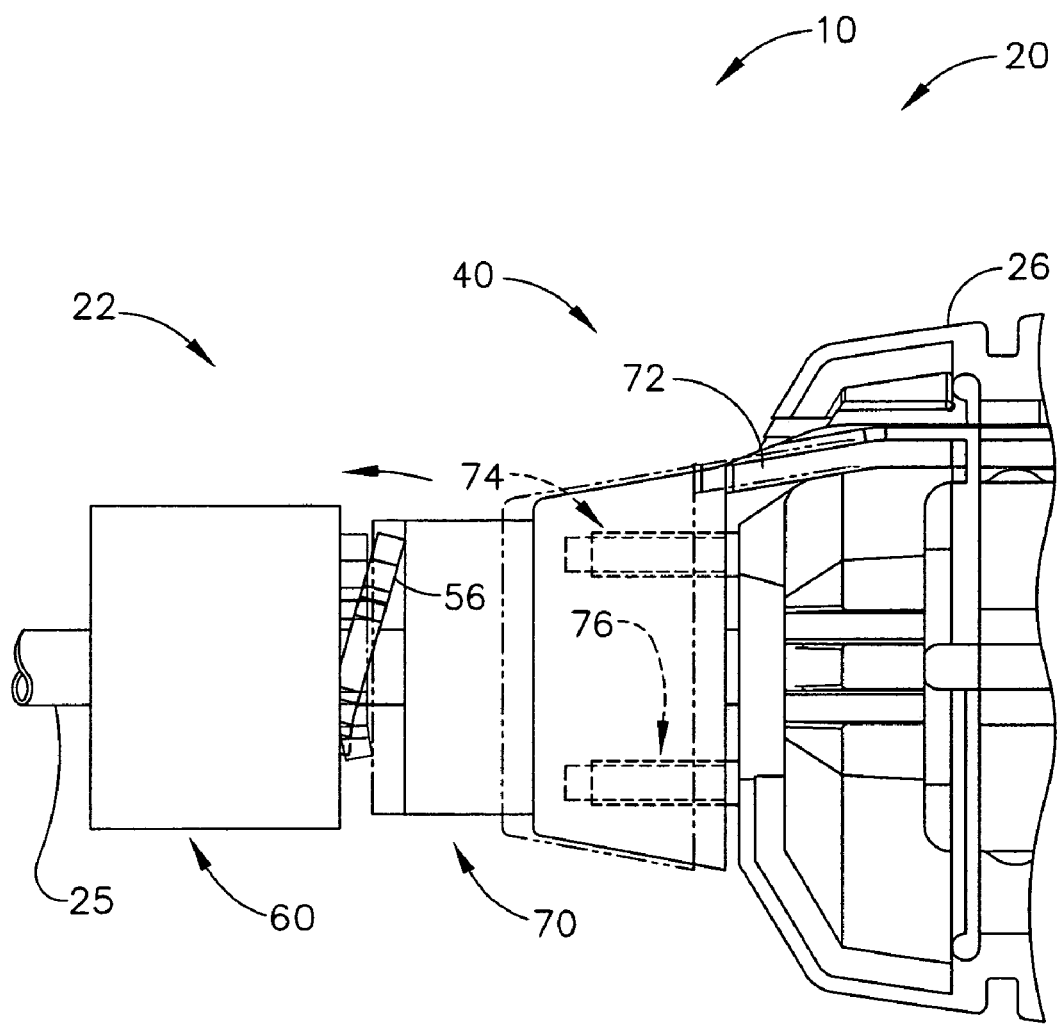
FIG. 3A is a right side detail view of an electrically and mechanically actuated anti-backup cam tube of FIG. 3 with an actuated (unlocked) position shown in phantom.
Figure 4:
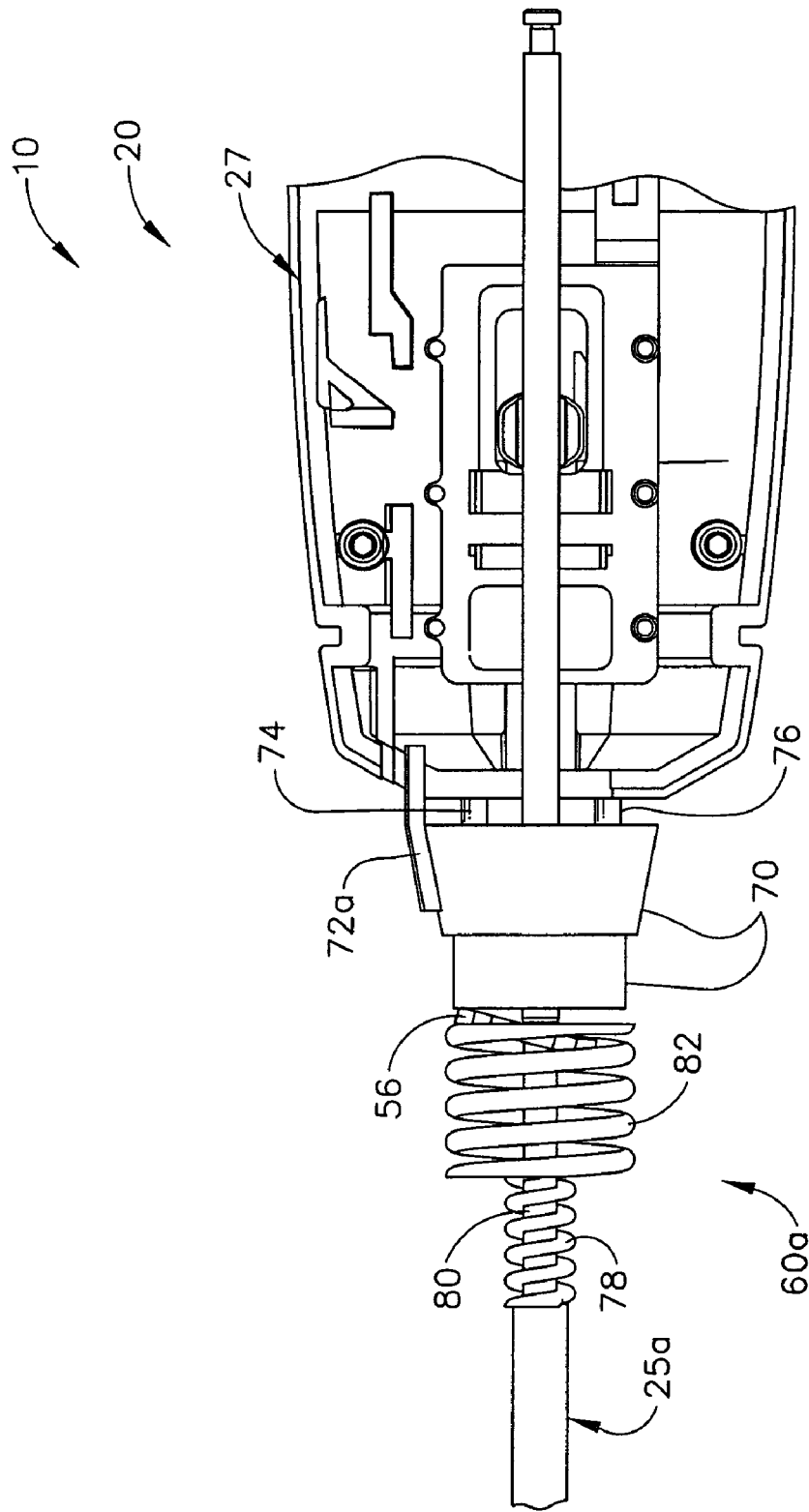
FIG. 4 is left side view of another version of the electrically actuated anti-backup mechanism of FIG. 1 with a spring biased locking plate and EAP-actuated anti-backup cam tube.
Figure 6:
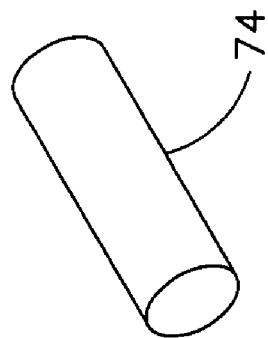
FIG. 6 is a perspective view of one EAP actuator of FIGS. 4-5.
Figure 5:
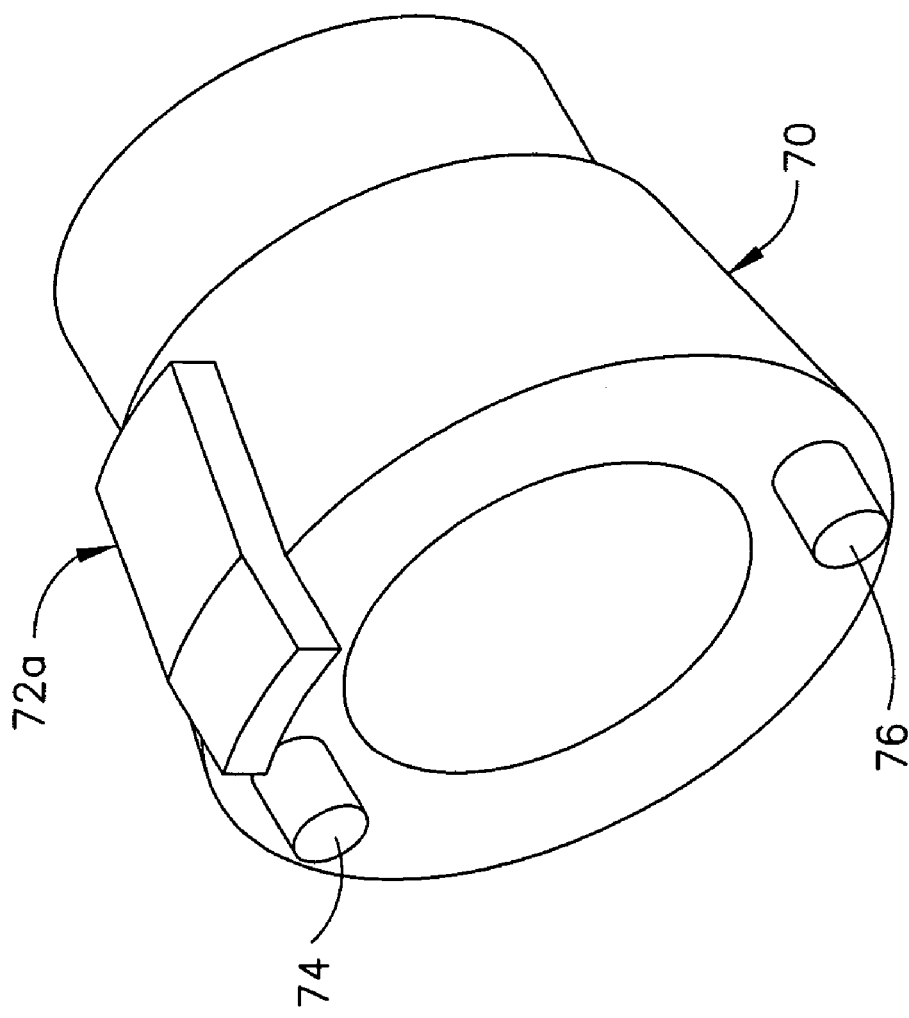
FIG. 5 is an aft perspective view of the EAP-actuated anti-backup cam tube of FIG. 4.
Figure 7:
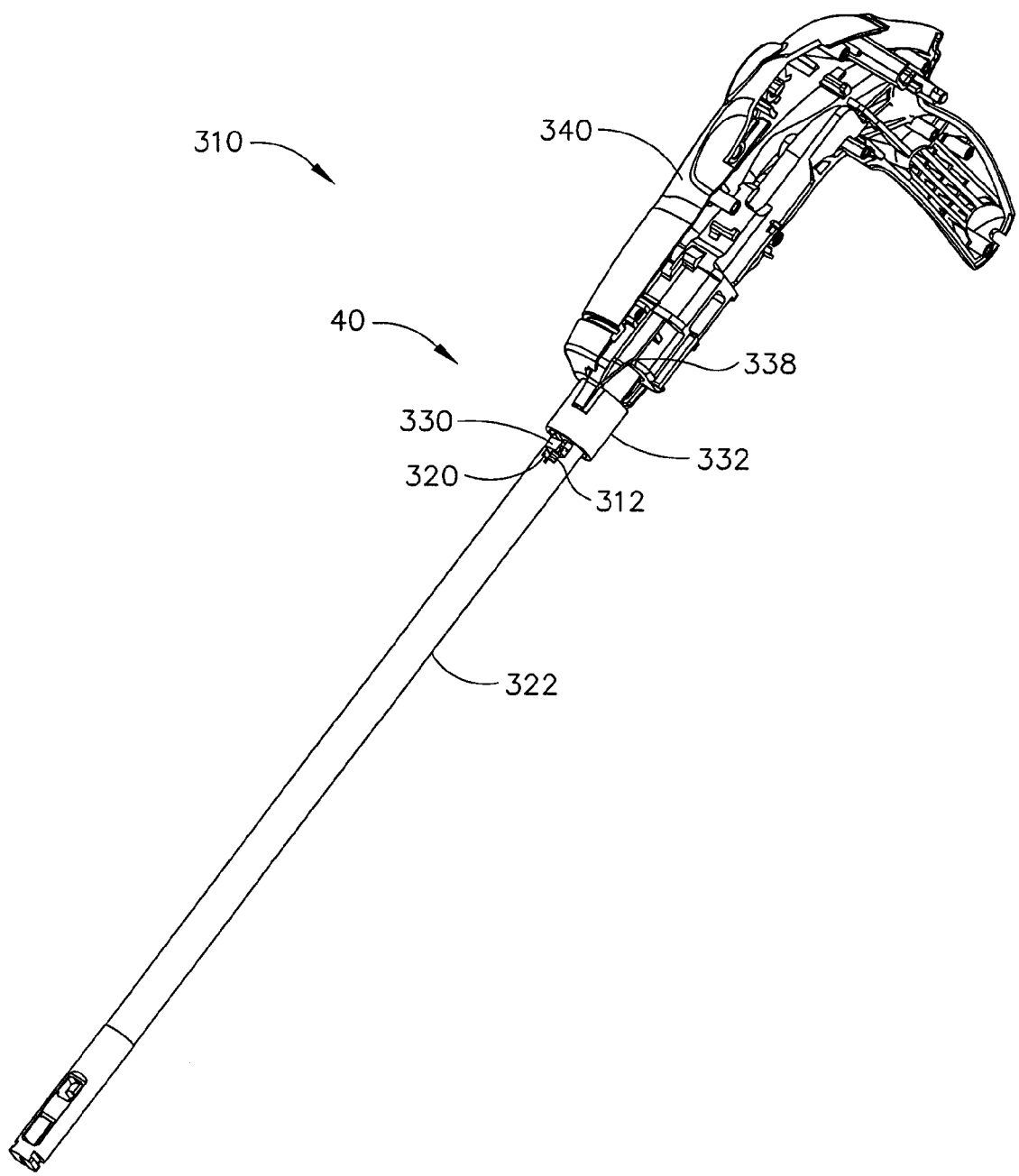
FIG. 7 is a top left perspective view of a frame ground, left half shell of a handle housing and another version of the electrically actuated anti-backup mechanism of FIG. 1 incorporating an EAP released binding coil.
Figure 16:
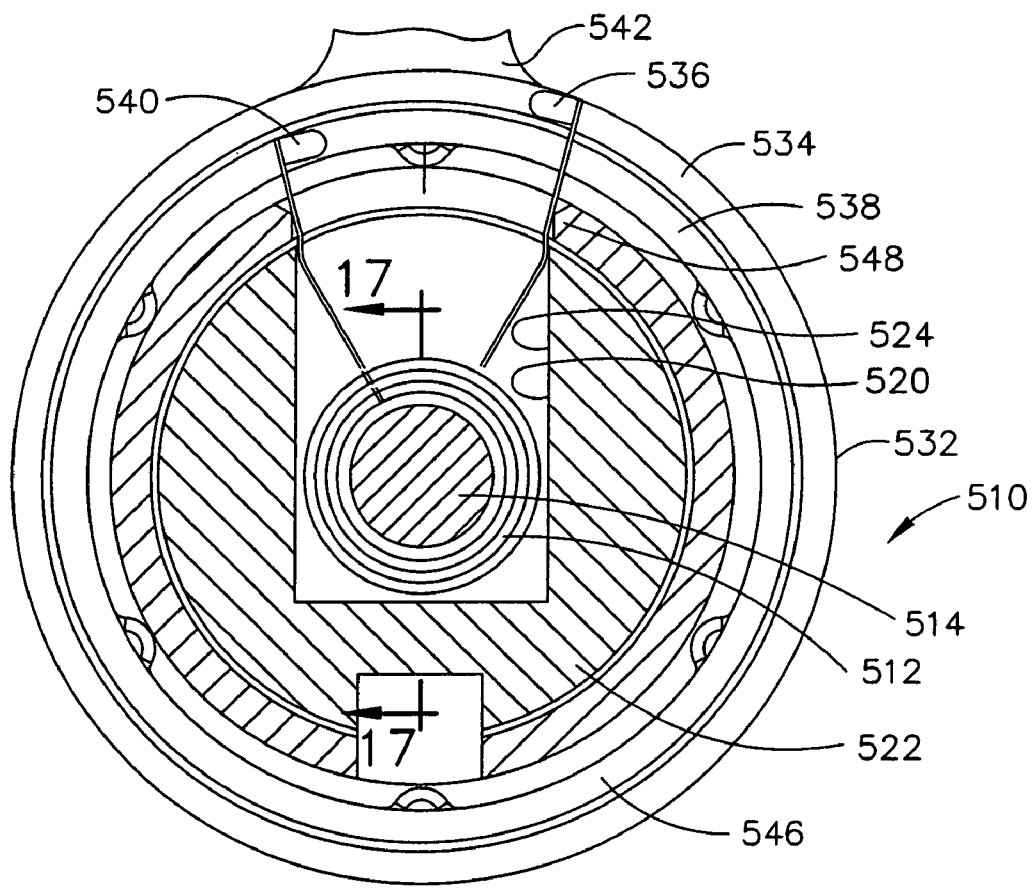
FIG. 16 is a front view taken in transverse cross section through the elongate shaft and an electrically actuated anti-backup mechanism of FIG. 14 taken along lines 14-14 with an alternative EAP cylindrical sleeve (contract to lock).
Figure 17:
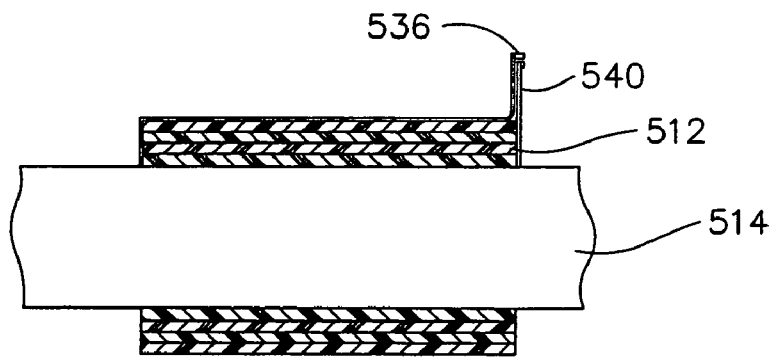
FIG. 17 is a left side detail view taken in longitudinal cross section through the contract-to-lock EAP cylindrical sleeve and firing rod of FIG. 16 taken along lines 17-17.

In FIG. 1, a surgical device suitable for endoscopic and laparoscopic use is depicted that advantageously combines a multiple firing stroke, automatic retraction of firing components, and an advantageously electrically actuated anti-backup mechanism consistent with the present invention to prevent inadvertent retraction between firing strokes. In FIGS. 2-3, 3A a version of the anti-backup mechanism of FIG. 1 is depicted. In particular, an electrical-mechanical (hybrid) anti-backup mechanism modifies the wholly mechanical implementation described in more detail in the afore-mentioned U.S. patent application Ser. Nos. 11/052,387 and 11/052,632, both of which more fully explain closure and firing operations of the handle common to the illustrative versions herein. In FIGS. 4-6, a version of the electrically actuated anti-backup mechanism further omits the mechanical portions for the mechanical end of firing travel and manual release of an anti-backup mechanism, relying solely upon a spring-biased locking plate for preventing retraction opposed by an electroactive polymer (EAP) actuated anti-backup cam tube for release similar to that depicted in FIGS. 2-3, 3A. In FIGS. 7-11, a version of the electrically actuated anti-backup mechanism employs a coil closely wound to bind the firing mechanism that is loosened by an EAP actuator to release. In FIGS. 12-15, a version of the electrically actuated anti-backup mechanism employs an EAP split cylindrical sleeve that expands to lock, being forced inwardly into binding contact with the firing rod by an encompassing shell and contracts to unlock. In FIGS. 16-17, a version of the electrically actuated anti-backup mechanism employs an EAP cylindrical sleeve that contracts inwardly into binding contact with the firing rod and expands to unlock.

Turning to the Drawings wherein like numerals denote like components throughout the several views, in FIG. 1, a surgical stapling and severing instrument 10 includes multi-stroke firing of an end effector, which in the illustrative version is a staple applying apparatus 12. An anvil 14 may be repeatably opened and closed about its pivotal attachment to an elongate (staple) channel 16. The staple applying assembly 12 is proximally attached to elongate shaft 18, which in turn is proximally attached to a handle. 20. In particular, a frame ground 21 of the elongate shaft 16 is rotatably engaged to the handle 20 at its proximal end and attached to the staple channel 16 at its distal end. The shaft 18 and staple applying apparatus 12 together form an implement portion 22. The staple applying assembly 12 is closed by distally advancing a closure tube 24 that encompasses the frame ground 21. The closed staple applying assembly 22 of the implement portion 22 presents a small cross-sectional area suitable for insertion through a cannula of a trocar (not shown) by externally manipulating the handle 20. With the implement portion 22 positioned, the staple applying assembly 12 is subsequently closed and clamped upon tissue. A firing member, depicted as a firing rod 25, is distally advanced within the frame ground 21 to effect severing and stapling within the staple applying assembly 12.

The handle 20 has user controls mounted on its handle housing 26 such as a rotation knob 27 that rotates the implement portion 22 about a longitudinal axis of the shaft 18. A closure trigger 28, which pivots in front of a pistol grip 30 about an attachment to the handle housing 27, is depressed to close the staple applying assembly 12 by distally moving the closure tube 24. A multiple stroke firing trigger 32, which pivots in front of the closure trigger 28, causes the staple applying assembly 12 to simultaneously sever and staple tissue clamped therein by distally advancing the firing rod 25. Since multiple firing strokes are employed to reduce the amount of force required per stroke by the surgeon's hand, right and left indicator wheels 34, 36 (the latter depicted in FIG. 2) rotate presenting indicia of the firing progress. For instance, full firing travel may require three full firing strokes and thus the indicator wheels 34, 36 rotate up to one-third of a revolution each per stroke. A manual retraction lever 38 allows retraction before full firing travel by manually disengaging a mechanical-electrical hybrid anti-backup mechanism 40 if desired and may further provide assistance to retract in the presence of binding or a failure in a retraction bias. A closure release button 41 is outwardly presented when the closure trigger 28 is clamped and partial firing has not occurred that would prevent unclamping the closure trigger 28.

A retraction bias in the handle 20 retracts the firing rod 25 after firing. When the firing trigger is released for another stroke, the anti-backup mechanism 40 engages the firing rod 25 to prevent inadvertent retraction. Advantageously, an anti-backup electrical actuator 42 is positioned proximate to the firing rod 25 for selectively moving between a locking and an unlocking state. A control module 44 activates the anti-backup electrical actuator 42. Electrical power may be provided by external power or as a depicted battery 46 connected to the control module 44 via a power button 48, which illuminates when activated. The control module 44 monitors operation of the surgical severing and stapling instrument 10 to determine when to lock and unlock firing, such as illustrated by a firing release sensor 50, depicted in phantom as a magnetic target 52 on an upper portion of the firing trigger 32 that moves relative to a Hall effect transducer 54 mounted inside of the handle housing 26. It should be appreciated that other sensors may be employed to sense conditions that would warrant locking or releasing the firing rod 25.

A version of the anti-backup mechanism 40 of FIG. 1 is depicted in FIGS. 2-3 that includes an anti-backup locking plate 56 with a through hole 66 (FIG. 2) that tips a top 58 of the locking plate 56 forward to a transverse nonbinding ("unlocked") position when the firing rod 25 distally advances and tips top 58 aft to an angled, binding ("locked") position when the firing rod 25 attempts to retract, assisted by a resilient member 60 that encompasses the firing rod 25 and is positioned distal to the locking plate 56. A lower tab attachment 62 (FIG. 2) extends proximally from a lower lip 64 of the proximal end of the frame ground 21, extending through an aperture (not shown) on a lower edge of the anti-backup locking plate 56. This lower tab attachment 62 draws the lower portion of the anti-backup locking plate 56 proximate to the frame ground 21 so that the anti-backup locking plate 56 is perpendicular when the firing rod 25 is distally advanced and allowed to tip top 58 aft into a binding state when the firing rod 25 attempts to retract.

An anti-backup resilient biasing member 68 encompasses the firing rod 25 and is positioned distal to the locking plate 56. Engagement between the biasing member 68 and locking plate 56 is limited to abutment between top edges of both to urge the locking plate 56 top back to lock. A distal side of the biasing member 68 abuts the frame ground 21, permitting expansion thus only proximally. On the proximal side of the locking plate 56, an anti-backup cam tube 70 encompasses the firing rod 25 and is constrained to move longitudinally. In particular, a proximally directed anti-backup cam yoke 72 is attached to a top proximal surface of the anti-backup cam tube 70 and is slidingly received into the handle housing 26, constraining rotation motion and serving in this version as a mechanical release actuator. The anti-backup cam tube 70 itself may be distally advanced by the anti-backup cam yoke 72 but advantageously may also be advanced by a pair of electrical actuators, depicted as EAP cylindrical actuators 74, 76. The anti-backup cam tube 70 and EAP cylindrical actuators 74, 76 are common to a version of the anti-backup mechanism 40 in FIGS. 4-6 wherein a shortened cam yoke 72a serves only to guide the anti-backup cam tube 70 and is not coupled for mechanical actuation for release. With reference to FIG. 3A, it is contemplated that passive and/or active biasing of the locking plate 56 may be incorporated by selecting one of several configurations. The anti-backup cam yoke 72 serves to communicate a mechanical release motion by either manual user input or automatic end of firing travel is provided.

The version of FIG. 4 differs in that the resilient member 60 comprises an anti-backup compression spring 60a having a narrow distal coil 78 that grips and is distally constrained by a narrowed portion 80 of a firing rod 25a. The anti-backup compression spring 60a also has a widened proximal coil 82 sized to contact the anti-backup locking plate 56. Thus, the anti-backup compression spring 60a provides a full-time locking bias that is overcome by distal movement of the firing rod 25a or the anti-backup cam tube 72a.

In FIG. 3A, the EAP actuators 74, 76 have a relaxed, contracted shape which allows the proximal urging of the resilient member 60 against the anti-backup locking plate 56 to push the anti-backup cam tube 70 proximally to the handle housing 26. When the EAP actuators 74, 76 are energized, the EAP actuators 74, 76 longitudinally expand as depicted in phantom, distally advancing the anti-backup cam tube 70, also depicted in phantom. It is contemplated that the version of FIG. 2-3, 3A may be configured with the resilient member 60 formed from an EAP actuator having a relaxed, contracted state and an activated, expanded state (e.g., a cylindrical stacked EAP laminate with a through hole configured to longitudinally expanded when electrically stimulated). Thus, the locking bias may be selectively removed to reduce the force to fire. The firing trigger 32 requires less force to move the locking plate 56 against the resilient member 60. Alternatively, the resilient member 60 may have a relaxed contracted state and an activated expanded state. Moreover, the resilient member 60 may be a combination compression spring longitudinally wrapped in EAP fiber actuators or be assisted and/or constrained by an EAP stacked laminate actuator.

Electroactive polymers (EAPs) are a set of conductive doped polymers that change shape when electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential ranges from 1V to 4 kV, depending on the polymer and ionic fluid used. Some of the EAPs contract when voltage is applied and some expand. The EAPs may be paired to mechanical means such as springs or flexible plates to change the effect caused when the voltage is applied.

There are two basic types and multiple configurations of each type. The two basic types are a fiber bundle and a laminate version. The fiber bundle consists of fibers around 30-50 microns. These fibers may be woven into a bundle much like textiles and are often called EAP yarn because of this. This type of EAP contracts when voltage is applied. The electrodes are usually a central wire core and a conductive outer sheath, which also serve to contain the ionic fluid that surrounds the fiber bundles. An example of a commercially available fiber EAP material is manufactured by Santa Fe Science and Technology, sold as PANION fiber and described in U.S. Pat. No. 6,667,825, which is hereby incorporated by reference in its entirety.

The other type is a laminate structure. It consists of a layer of EAP polymer, a layer of ionic gel and two flexible plates that are attached to either side of the laminate. When a voltage is applied, the square laminate plate expands in one direction and contracts in the perpendicular direction. An example of a commercially available laminate (plate) EAP material is available from Artificial Muscle Inc, a division of SRI Laboratories. Plate EAP material is also available from EAMEX of Japan and referred to as thin film EAP.

It should be noted that EAPs do not change volume when energized; they merely expand or contract in one direction while doing the opposite in the transverse direction. The laminate version may be used in its basic form by containing one side against a rigid structure and using the other much like a piston. It may also be adhered to either side of a flexible plate. When one side of the flexible plate EAP is energized, it would expand, flexing the plate in the opposite direction. This allows the plate to be flexed either direction depending on which side is energized.

An EAP actuator usually consists of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve will form the other electrode for the actuator as well as contain the ionic fluid necessary for the function of the device. In this configuration when the electrical field is applied to the electrodes, the strands of EAP shorten. This configuration of the EAP actuator is called a fiber EAP actuator. Likewise, the laminate configuration may be placed in numerous layers on either side of a flexible plate or merely in layers on itself to increase its capabilities. Typical fiber structures have an effective strain of 2-4% where the typical laminate version achieves 20-30%, utilizing much higher voltages. It should be appreciated, however, that these performance ranges are not determinative.

For instance, a laminate EAP composite may be formed from a positive plate electrode layer attached to an EAP layer, which in turn is attached to an ionic cell layer, which in turn is attached to a negative plate electrode layer. A plurality of laminate EAP composites may be affixed in a stack by adhesive layers therebetween to form an EAP plate actuator. It should be appreciated that opposing EAP actuators may be formed that can selectively bend in either direction.

A contracting EAP fiber actuator may include a longitudinal platinum cathode wire that passes through an insulative polymer proximal end cap, and then through an elongate cylindrical cavity formed within a plastic cylinder wall that is conductively doped to serve as a positive anode. A distal end of the platinum cathode wire is embedded into an insulative polymer distal end cap. A plurality of contracting polymer fibers are arranged parallel with and surrounding the cathode wire and have their ends embedded into respective end caps. The plastic cylinder wall is peripherally attached around respective end caps to enclose the cylindrical cavity to seal in ionic fluid or gel that fills the space between contracting polymer fibers and cathode wire. When a voltage is applied across the plastic cylinder wall (anode) and cathode wire, ionic fluid enters the contracting polymer fibers, causing their outer diameter to swell with a corresponding contraction in length, thereby drawing the end caps toward one another.

In FIGS. 2-3, the components of the handle 20 common to the afore-mentioned U.S. patent application Ser. Nos. 11/052, 387 and 11/052,632 effect closure and firing and mechanical actuation of the anti-backup cam tube 72. The frame ground 21 is rotatably engaged to the handle 20 so that twisting the rotation knob 27 causes rotation of the implement portion 22. Each half shell of the rotation knob 27 includes an inward projection 90 (FIG. 2) that enters a respective longer side opening 92 in the closure tube 24 and moves inward to engage the frame ground 21 that determines the rotated position of the implement portion 22. The longitudinal length of the longer openings 92 is sufficiently long to allow longitudinal closure motion of the closure tube 24.

The closure trigger 28 rotates about a closure trigger pin 93 that is laterally engaged within the handle housing 26. An upper portion 94 of the closure trigger 28 above the closure trigger pin 95 pushes forward a closure yoke 96 via a closure link 98. The closure link 98 is pivotally attached at its distal end by a closure yoke pin 100 to the closure yoke 96 and is pivotally attached at its proximal end by a closure link pin 102. The closure trigger 28 is urged to the open position by a closure trigger tension spring 104 that is connected proximally to the upper portion 94 of the closure trigger 28 and to the handle housing 26.

The upper portion 94 of the closure trigger 28 includes a proximal crest 106 with an aft notch 108. The closure release button 41 and a pivoting locking arm 110 are connected by a central lateral pivot 112. A compression spring 114 biases the closure release button 41 proximally (clockwise about the central lateral pivot 112 as viewed from the right), With the upper portion 94 back when the closure trigger 28 is released, the pivoting locking arm 110 rides upon the proximal crest 106 drawing in the closure release button 41. When the closure trigger 28 reaches its fully depressed position, it should be appreciated that the aft notch 108 is presented below the pivoting locking arm 110, which drops into and locks against the aft notch 108 under the urging of the compression spring 114. With the firing components retracted, manual depression of the closure release button 41 rotates the pivoting locking arm 110 upward, unclamping the closure trigger 28.

Once the closure trigger 28 is proximally clamped, the firing rod 25 is distally moved from the handle 20 in response to the multiple stroke firing trigger 32 being drawn to the pistol grip 30 with the amount of firing travel visible to the surgeon on the right and left indicator wheels 34, 36. The firing trigger 32 pivots about a firing trigger pin 118 that laterally traverses and is engaged laterally across the handle housing 26.

A linked transmission firing mechanism 120 is initially retracted, urged to remain in this position by a combination tension/compression spring 122 that is constrained within the pistol grip 30 of the handle 20, with its nonmoving end 124 connected to the housing 26 and a moving end 126 connected to a downwardly flexed and proximal, retracted end 128 of a steel band 130.

A distally-disposed end 132 of the steel band 130 is attached to an attachment feature 134 on a front link 136a of a plurality of links 136a-136d that form a linked rack 140. A rack guide tube 141 has a proximally open internal cavity 142 shaped to receive the plurality of links 136a-136d when distally advanced and a smaller distal opening 143 shaped to allow the passage of the firing rod 25 that is attached to the distal most link 136a. Left and right gripping features 144, 145 extend inwardly in opposition from the handle housing 26 through elongate slots 146, 147 respectively in the closure yoke 96 and a rack channel cover 148 to engage a respective proximal side recess 149 formed in the rack guide tube 141. Thereby, a linked rack 140 is flexible yet has proximal links that form a straight rigid rack assembly that may transfer a significant firing force through the firing rod 25 in the implement portion 22, yet readily retracts into the pistol grip 30 to minimize the longitudinal length of the handle 20. It should be appreciated that the combination tension/compression spring 122 increases the amount of firing travel available while essentially reducing the minimum length by half over a single spring.

As mentioned, the anti-backup cam yoke 72 is moved to effect mechanical release of the anti-backup locking plate 56. Automatic triggering is based upon the distal link 136d including a tang 150 that projects upwardly when the distal link 136d is advanced into a rack channel 152 formed in the closure yoke 96. This tang 150 is aligned to activate a bottom proximal cam 154 on an anti-backup release lever 156. Structures formed in the handle housing 26 constrain movement of the anti-backup release lever 156. A pin receptacle 158 and circular pin 160, formed respectively between right and left half shells of the handle housing 26, is received through a longitudinally elongate aperture 162 formed in the anti-backup release lever 156 distal to the bottom proximal cam 154, thus allowing longitudinal translation as well as rotation about the circular pin 160. In the right half shell of the handle housing 26, a proximally open channel 164 includes a proximal horizontal portion 166 that communicates with an upwardly and distally angled portion 168 that receives a rightward aft pin 170 near the proximal end of the anti-backup release lever 156, thus imparting an upward rotation as the anti-backup release lever 156 reaches the distal most portion of its translation. A blocking structure 172, formed in the right half shell of the handle housing 26 proximal to the anti-backup release lever 156, prevents proximal movement thereof once assembled to maintain rightward aft pin 170 in the proximally open channel 164.

A distal end 174 of the anti-backup release lever 156 thus is urged distally and downwardly, causing a rightward front pin 176 to drop into distally open step structure 178 formed in the right half shell of the handle housing 26, which is urged into this engagement by a compression spring 180 hooked to a leftward hook 182 on the anti-backup release lever 156 between the rightward front pin 176 and the longitudinally elongate aperture 162. The other end of the compression spring 180 is attached to a hook 184 formed in the right half shell of the handle housing 26 in a more proximal and lower position just above the closure yoke 96. The compression spring 180 thus pulls the distal end 174 of the anti-backup release lever 156 down and aft, which results in the rightward front pin 176 locking into the distally open step structure 178 when distally advanced.

Once tripped, the anti-backup release lever 156 remains forward holding the anti-backup locking plate 56 perpendicularly, thus allowing the linked rack 140 to be retracted. When the closure yoke 96 is subsequently retracted when unclamping the end effector 12, an upwardly projecting reset tang 186 on the closure yoke 96 contacts a bottom distal cam 188 of the anti-backup release lever 156, lifting the rightward front pin 176 out of the distally open step structure 178 so that the anti-backup resilient member 60 can proximally push the anti-backup cam tube 70 and the anti-backup release lever 156 to their retracted positions.

The firing trigger 32 pivots about the firing trigger pin 118, distally and proximally reciprocating an upper portion 190 of the firing trigger 32, stretching a proximally placed firing trigger tension spring 192 proximally connected between the upper portion 190 of the firing trigger 32 and the housing 26. The upper portion 190 of the firing trigger 32 engages the linked rack 140 during each firing trigger depression by a spring-biased side pawl mechanism 194 that also disengages when the firing trigger 32 is released.

In particular, a ramped right-side track 196 formed by a proximally and rightwardly facing beveled surface 198 in each of the links 136a-136d is engaged by a side pawl mechanism 194. In particular, a pawl slide (shuttle) 200 has right and left lower guides 202 that slide respectively in a left track 204 formed in the closure yoke 96 below the rack channel 152 and a right track 206 formed in a closure yoke rail 208 that parallels rack channel 152 and is attached to the rack channel cover 148 that closes a rightwardly open portion of the rack channel 152 in the closure yoke 96 that is distal to the travel of the pawl slide 200. In FIGS. 3, 6, a compression spring 212 is attached between a hook 214 on a top proximal position on the closure yoke rail 208 and a hook 216 on a distal right side of the pawl slide 200, which keeps the pawl slide 200 drawn proximally into contact with the upper portion 190 of the firing trigger 32.

A pawl block 218 sits on the pawl slide 200 pivoting about a vertical aft pin 220 that passes through a left proximal corner of pawl block 218 and pawl slide 200. A kick-out block recess 222 is formed on a distal portion of a top surface of the block 218 to receive a kick-out block 224 pivotally pinned therein by a vertical pin 226 whose bottom tip extends into a pawl spring recess 228 on a top surface of the pawl slide 200. A pawl spring 230 in the pawl spring recess 228 extends to the right of the vertical front pin 226, urging the pawl block 218 to rotate counterclockwise when viewed from above into engagement with the ramped right-side track 196. A small coil spring 232 in the kick-out block recess 222 urges the kick-out block 224 to rotate clockwise when viewed from above, its proximal end urged into contact with a contoured lip 234 formed in the closure yoke 96 above the rack channel 152.

The stronger mechanical advantage of the pawl spring 230 over the small coil spring 232 means that the pawl block 218 tends toward engagement with the kick-out block 224 rotated clockwise. As the firing trigger 32 is fully depressed and begins to release, the kick-out block 224 encounters a ridge 236 in the contoured lip 234 as the pawl slide 200 retracts, forcing the kick-out block 224 to rotate clockwise when viewed from above and thereby kicking out the pawl block 218 from engagement with the linked rack 140. The shape of the kick-out block recess 222 stops the clockwise rotation of the kick-out block 224 to a perpendicular orientation to the contoured lip 234, maintaining this disengagement during the full retraction and thereby eliminating a ratcheting noise.

As mentioned, the surgical stapling and severing instrument 10 includes a manual retraction capability that provides firing position indication, manual release of the firing mechanism and manual retraction of the linked rack 140. A front idler gear 240 engages a toothed upper, left surface 242 of the linked rack 140. The front idler gear 240 also engages an aft idler gear 244 having a smaller right-side ratchet gear 246. Both the front idler gear 240 and aft idler gear 244 are rotatably connected to the handle housing 26 respectively on front idler axle 248 and aft idler axle 250. Each end of the aft idler axle 250 extends through the respective right and left housing half shells of the handle housing 26 and is attached to the left and right indicator wheels 34, 36. Since the aft idler axle 250 is free spinning in the handle housing 26 and has a keyed engagement to the aft idler gear 244, the indicator wheels 34, 36 rotate with the aft idler gear 244. The gear relationship between the linked rack 140, front idler gear 240 and aft idler gear 244 may be advantageously selected so that the toothed upper surface 242 has tooth dimensions that are suitably strong and so that the aft idler gear 244 makes no more than one revolution during the full firing travel of the linked rack 140.

The smaller right-side ratchet gear 246 of the aft idler gear 244 extends into a hub 260 of the manual retraction lever 38, specifically aligned with a vertical longitudinally-aligned slot 262 bisecting the hub 260. A lateral through hole 264 of the hub 260 communicates with an upper recess 266. A front portion of the upper recess 266 is shaped to receive a proximally directed locking pawl 268 that pivots about a rightward lateral pin 270 formed in a distal end of the upper recess 266. An aft portion of the upper recess 266 is shaped to receive an L-shaped spring tab 272 that urges the locking pawl 268 downward into engagement with the right-side smaller ratchet gear 246. A hold-up structure 274 projects from the right half shell of the handle housing 26 into the upper recess 266, holding up the locking pawl 268 from engaging the smaller right-side ratchet gear 246 when the manual retraction lever 38 is down. A coil spring 276 urges the manual retraction lever 38 down. As the manual retraction lever 38 is raised, the locking pawl 268 rotates clockwise (when viewed from the right), and is no longer held up by the hold-up structure 274 and engages the smaller right-side ratcheting gear 246, rotating the aft idler gear 244 counterclockwise when viewed from the right. Thus, the forward idler gear 240 responds clockwise, retracting the linked rack 140. In addition, a rightward curved ridge 278 projects out from the hub 260, sized to contact and distally move the anti-backup release lever 156 to mechanically release the anti-backup mechanism 40 as the manual retraction lever 38 is rotated.

Figure 8:
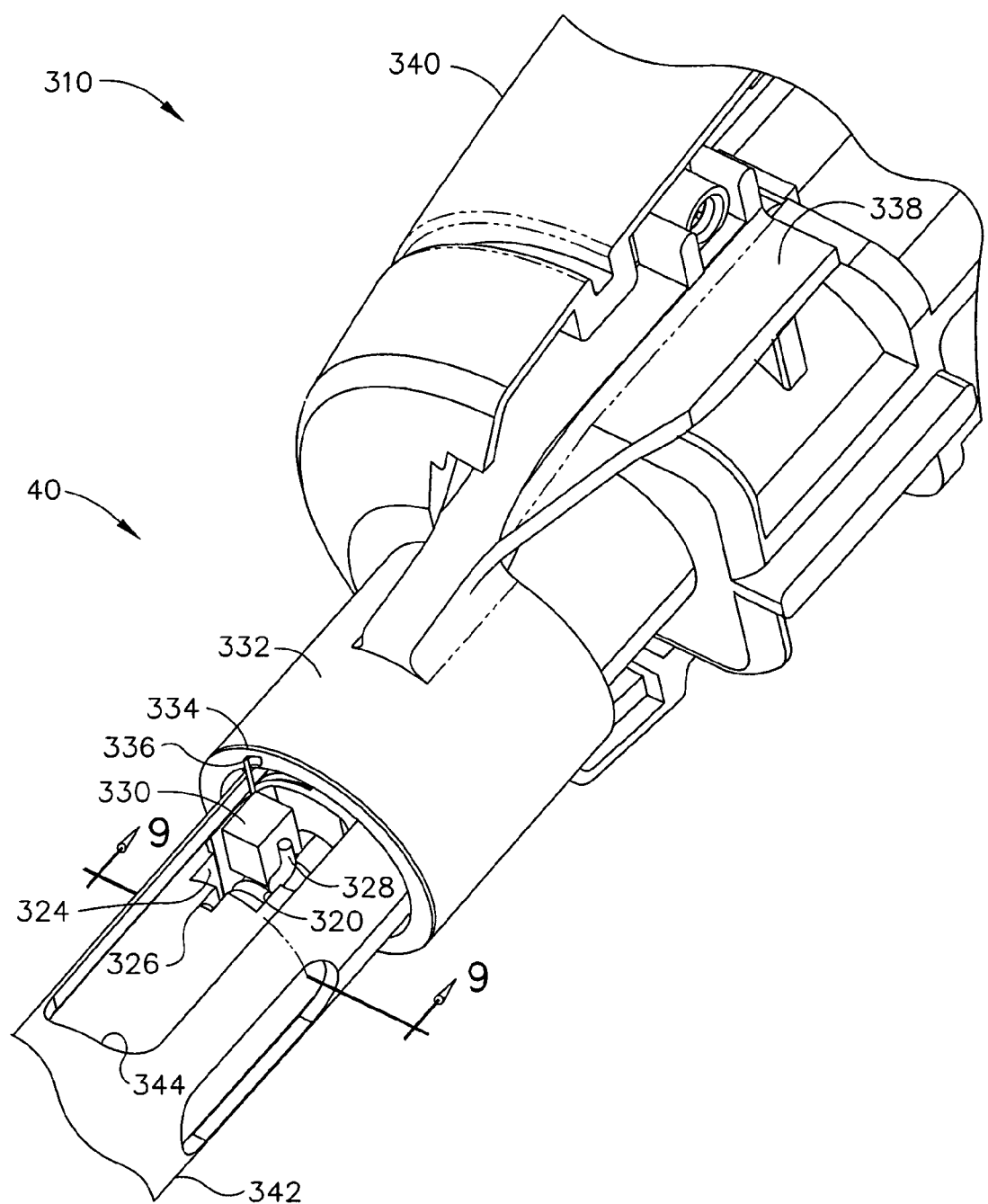
FIG. 8 is a top left perspective detail view of the EAP actuator and proximal portion of the anti-backup binding coil of the FIG. 7.
Figure 11:
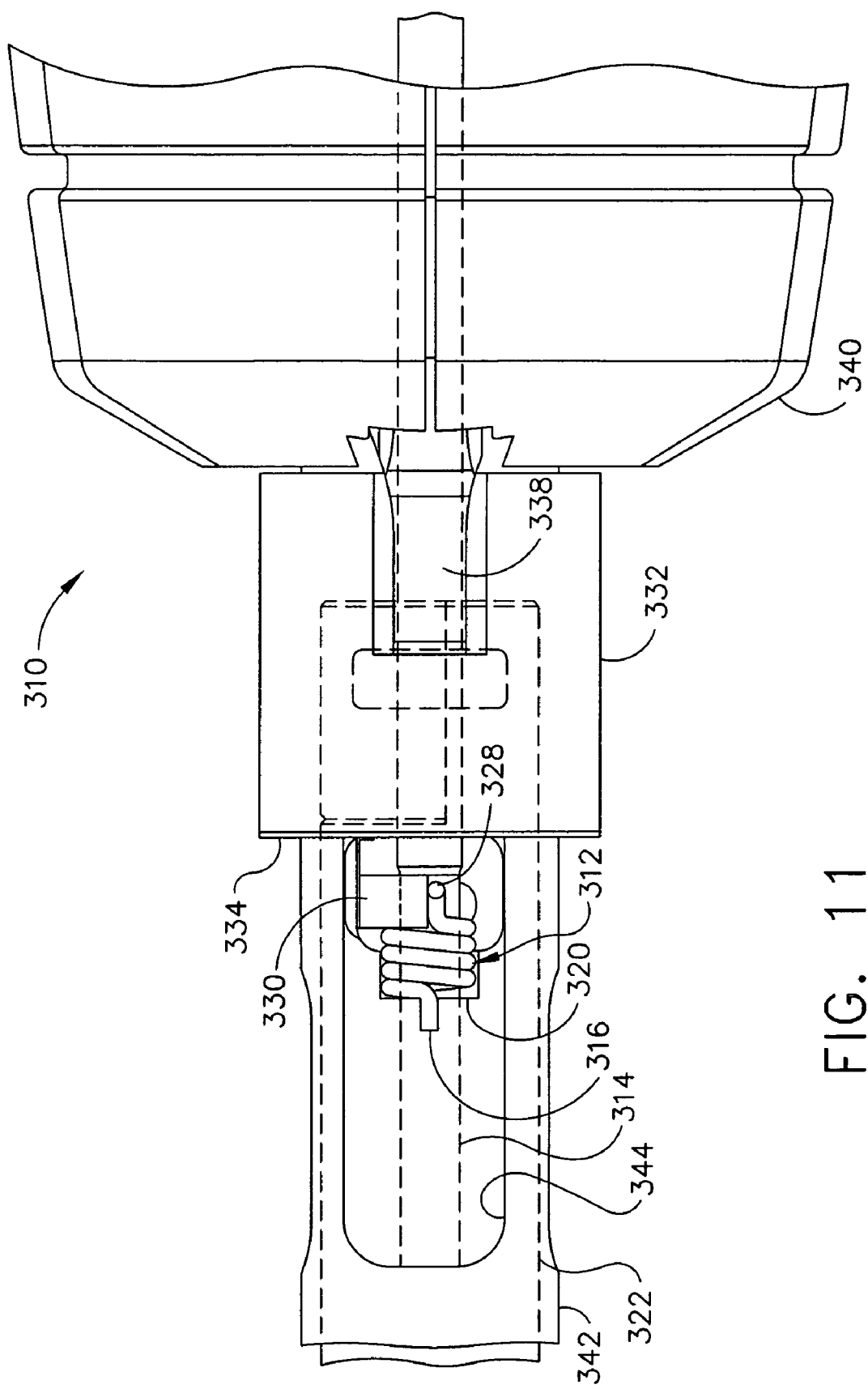
FIG. 11 is a left side detail view in elevation of the electrically actuated anti-backup mechanism of FIG. 7 with the frame ground and firing rod shown in phantom.

In FIGS. 7-11, a version of the electrically actuated anti-backup mechanism 40 for a surgical stapling and severing instrument 310 includes a wound anti-backup spring 312 that closely encompasses a firing rod 314. In particular, a distal end 316 of the wound anti-backup spring 312 extends longitudinally. With particular reference to FIG. 8, an upwardly open actuator recess 320 formed in a frame ground 322 includes a generally rectangular prism opening 324 with a distal vertical slot 326 that receives and prevents rotation of the distal end 316 of the wound anti-backup spring 312. A leftward vertical slot 328 of the upwardly open actuator recess 320 is aligned to receive an upturned proximal end 328 of the wound anti-backup spring 312 when rotated top leftward by an EAP block actuator 330 positioned against a right proximal side of the upwardly open actuator recess 320. In FIG. 11, the wound anti-backup spring 312 is coiled in a direction that tightens as the upturned proximal end 328 is rotated leftward. It should be appreciated that the energized state (e.g., laterally expanded, laterally contracted) of the EAP actuator 330 and the direction of tightening of the wound anti-backup spring 312 may be selected for biased locked or biased unlocked.

Alternatively, it should be appreciated that a wound spring (not shown) may be longitudinally shortened to a radially expanded, unlocked state and may be longitudinally extended to a radially contracted, locked state with an electrical actuator coupled across the length of the wound spring to effect this change. Alternatively, one end of the wound spring may be fixed relative to a frame ground and a free end of the wound spring may be moved by an electrical actuator relative to the frame ground to effect this change.

Figure 9:
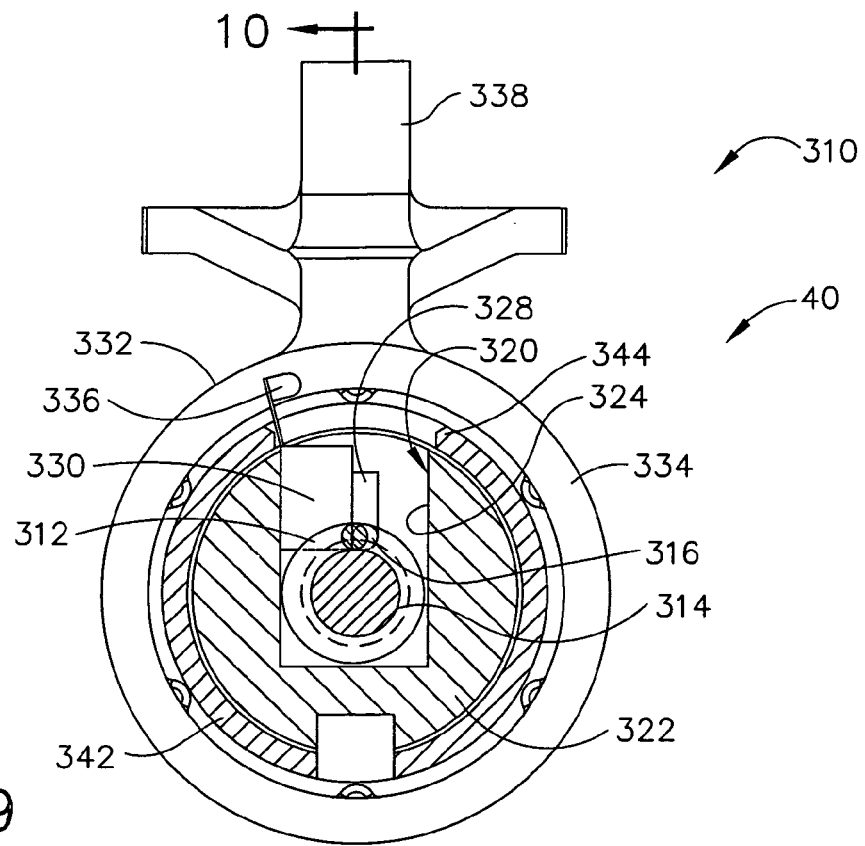
FIG. 9 is a front view taken in cross section through the EAP released binding coil along lines 9-9 of the electrically actuated anti-backup mechanism of FIG. 8.
Figure 10:
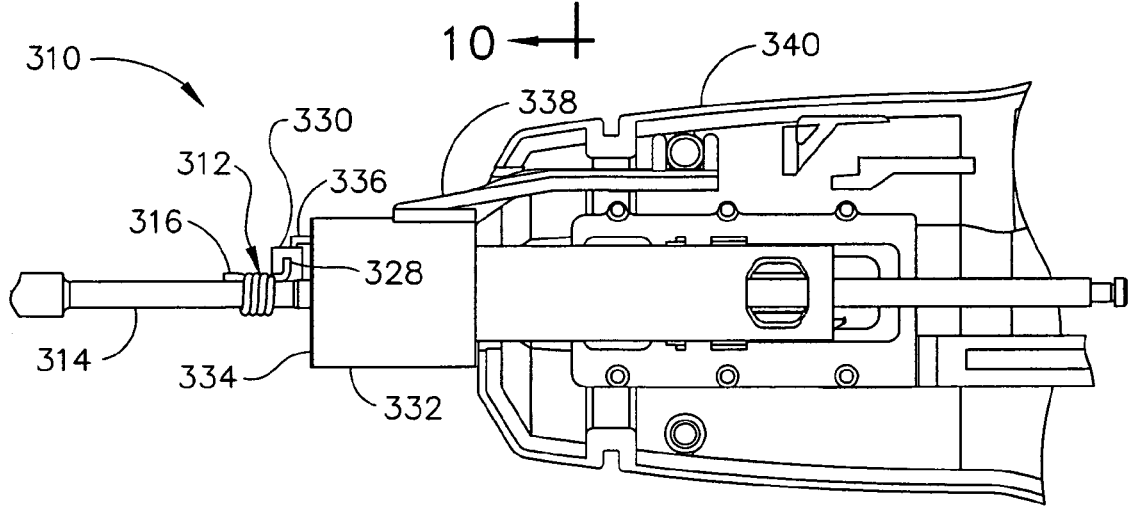
FIG. 10 is a left side view in elevation of electrically actuated anti-backup mechanism of FIG. 7 with the frame ground removed to expose the EAP released binding coil.

With particular reference to FIG. 8, a fixed collar 332 has a distal conducting circumferential ring 334 that is swiped by a contact 336 that serves as one electrode for the EAP block actuator 330 with an electrical ground path provided by the frame ground 322. In FIGS. 7-10, a proximally projecting arm 338 is attached to a top proximal surface of the fixed collar 332 and is engaged to a handle housing 340 to prevent rotation or longitudinal movement of the fixed collar 332. In FIGS. 8-9, a closure sleeve 342 has an elongate top aperture 344 sized to accommodate the extension of the contact 336 during closure translation. It should be appreciated that a rotation knob (not shown) overlies the elongate top aperture 344 of the closure sleeve 342 and the upwardly open actuator recess 320 in the frame ground 322.

Figure 12:
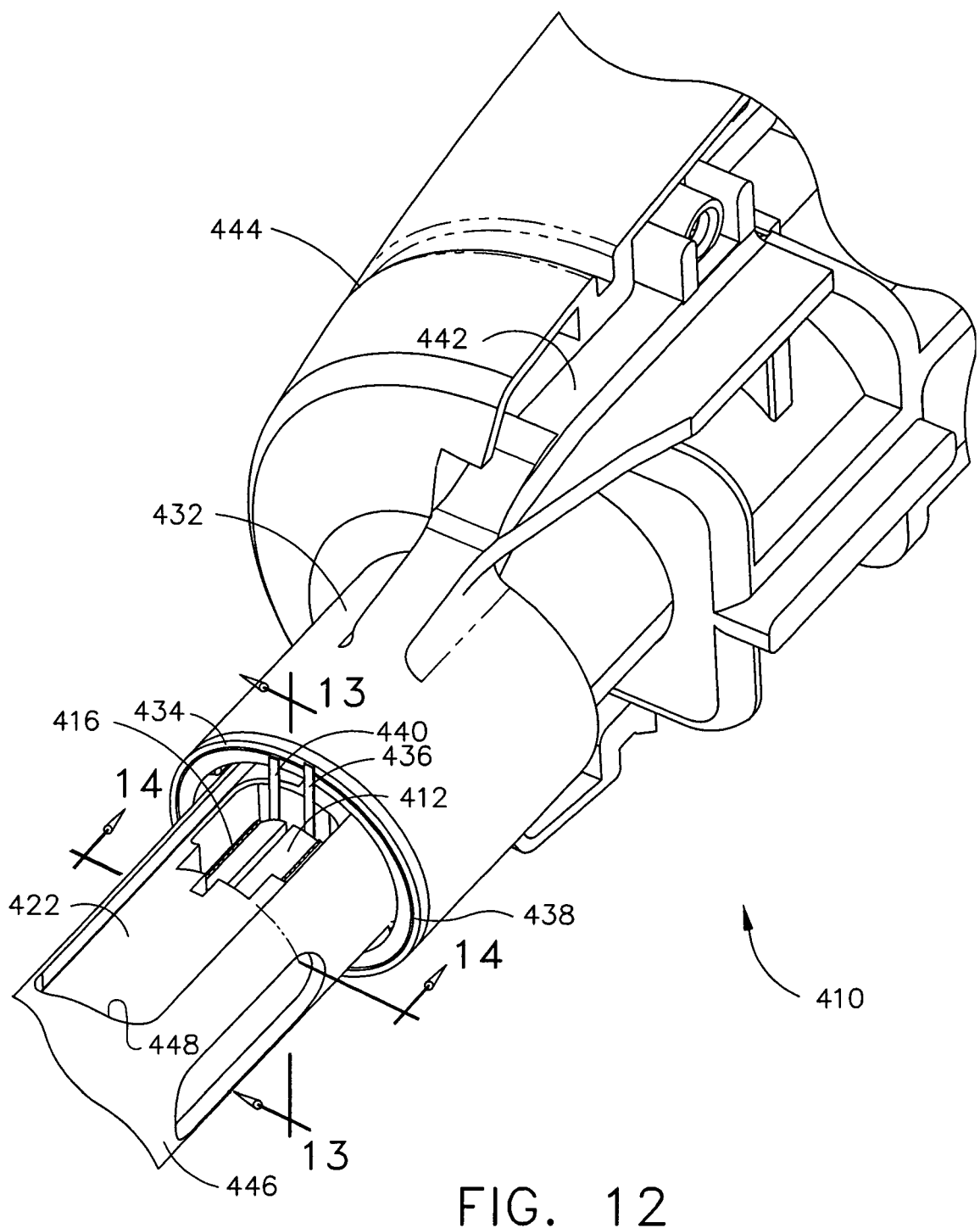
FIG. 12 is a top left perspective detail view of another version of the electrically actuated anti-backup mechanism of FIG. 1 including an EAP split cylindrical binding sleeve.
Figure 13:
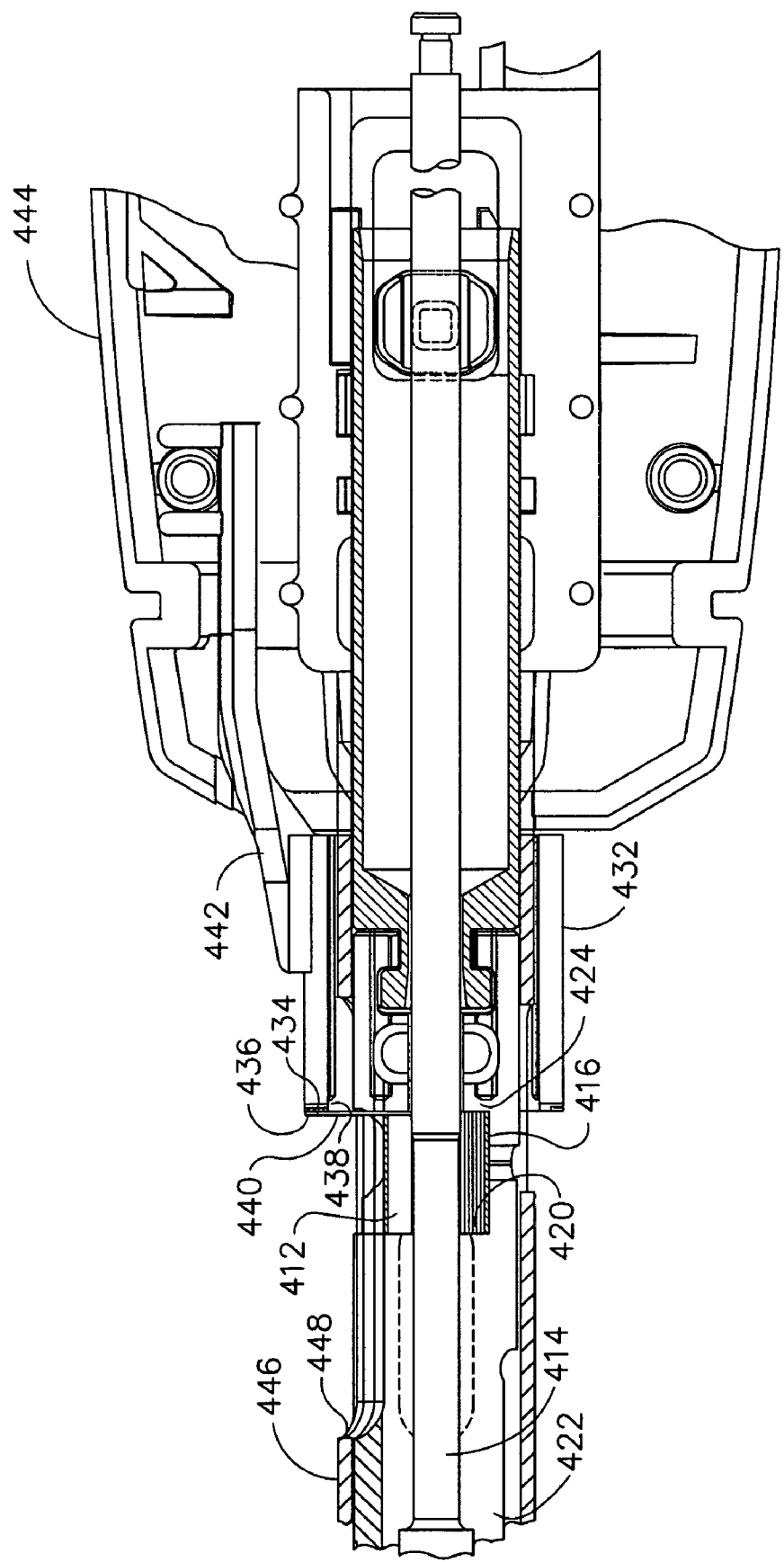
FIG. 13 is a left side view in longitudinal cross section taken in elevation through an elongate shaft and the electrically actuated anti-backup mechanism along lines 13-13 of FIG. 12.
Figure 14:
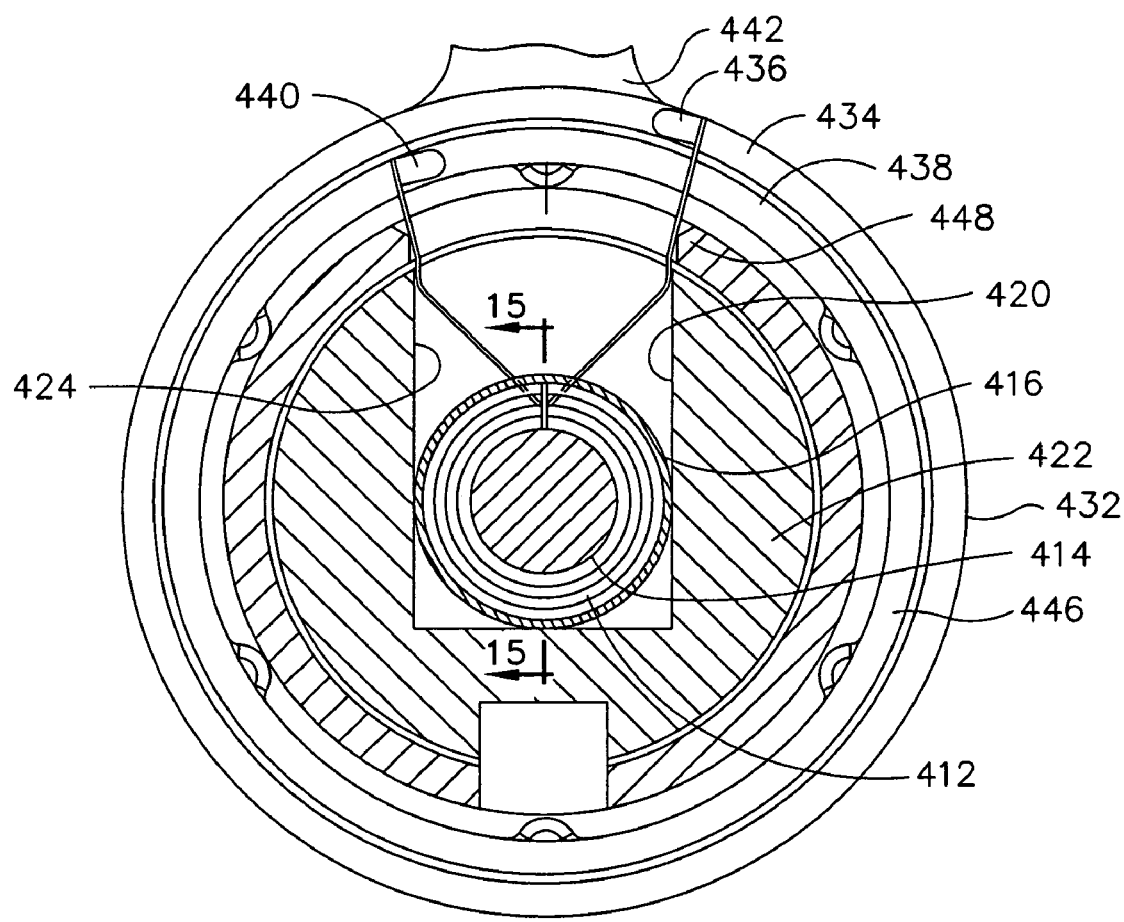
FIG. 14 is a front view taken in transverse cross section through the elongate shaft and EAP split cylindrical sleeve (expanded to lock) in a confining shell taken along lines 14-14 of FIG. 12.
Figure 15:
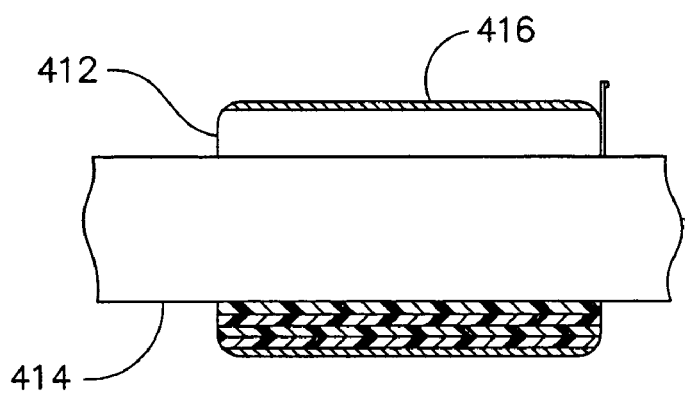
FIG. 15 is a left side detail view taken in longitudinal cross section through the expand-to-lock EAP split cylindrical sleeve and firing rod of FIG. 14 taken along lines 15-15.

In FIGS. 12-15, a version of the electrically actuated anti-backup mechanism 40 for a surgical stapling and severing instrument 410 includes an EAP split cylindrical actuator 412 that closely encompasses a firing rod 414 and radially expands when energized. A rigid sleeve 416 encompasses the EAP split cylinder actuator 412 forcing expansion inwardly into binding contact with the firing rod 414. With particular reference to FIG. 12, an upwardly open actuator recess 420 formed in a frame ground 422 includes a generally rectangular prism opening 424. A fixed collar 432 has an outer distal conducting circumferential ring 434 that is swiped by a first contact 436 and an inner distal conducting circumferential ring 438 that is swiped by a second contact 440 that serves as electrodes (i.e., cathode, anode) for the EAP split cylindrical actuator 412. A proximally projecting arm 442 is attached to a top proximal surface of the fixed collar 432 and is engaged to a handle housing 444 to prevent rotation or longitudinal movement of the fixed collar 432. In FIGS. 12-14, a closure sleeve 446 has an elongate top aperture 448 sized to accommodate the extension of the contacts 436, 440 during closure translation. It should be appreciated that a rotation knob (not shown) overlies the elongate top aperture 448 of the closure sleeve 446 and the upwardly open actuator recess 420 in the frame ground 422.

In FIGS. 16-17, a version of the electrically actuated anti-backup mechanism 40 for a surgical stapling and severing instrument 510 includes an EAP cylindrical actuator 412 that closely encompasses a firing rod 514, having a relaxed, contracted state that forms a binding contact with the firing rod 514 and radially expands when energized out of binding contact. An upwardly open actuator recess 520 formed in a frame ground 522 includes a generally rectangular prism opening 524. A fixed collar 532 has an outer distal conducting circumferential ring 534 that is swiped by a first contact 536 and an inner distal conducting circumferential ring 538 that is swiped by a second contact 540 that serves as electrodes (i.e., cathode, anode) for the EAP split cylindrical actuator 512. A proximally projecting arm 542 is attached to a top proximal surface of the fixed collar 532 and is engaged to a handle housing (not shown) to prevent rotation or longitudinal movement of the fixed collar 532. In FIG. 16, a closure sleeve 546 has an elongate top aperture 548 sized to accommodate the extension of the contacts 536, 540 during closure translation. It should be appreciated that a rotation knob (not shown) overlies the elongate top aperture 548 of the closure sleeve 546 and the upwardly open actuator recess 520 in the frame ground 522.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

It will be appreciated that the terms "proximal" and "distal" are used herein with reference to a clinician gripping a handle of an instrument. Thus, the end effector 12 is distal with respect to the more proximal handle 20. Analogous terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these terms are not intended to be limiting and absolute.

The present invention is being discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

Applications consistent with the present invention may include single firing stroke instruments as well as those with a solid firing rack rather than a linked rack.

As another example, a rocking boot type anti-backup lever may be positioned into binding contact. A manual rocking boot type anti-backup lever is disclosed in U.S. patent application Ser. No. 10/881,105, "SURGICAL STAPLING INSTRUMENT INCORPORATING A MULTISTROKE FIRING MECHANISM HAVING A ROTARY TRANSMISSION" to Whitacre et al., filed on 30 Jun. 2004, the disclosure of which is hereby incorporated by reference in its entirety.

What is claimed is:

1. A surgical instrument, comprising:
   an end effector;
   a longitudinally reciprocating firing member distally coupled to the end effector;
   a shaft having a distal end attached to the end effector and operatively configured to guide the firing member;
   a handle attached to a proximal end of the shaft operatively configured to distally advance the firing member in a sequence of strokes; and
   an electrical actuator physically grounded to the handle and responsive to an electrical signal to move between a non-binding and a binding position with the firing member to prevent longitudinal movement thereof, wherein the electrical actuator comprises an electroactive polymer actuator;
   wherein the shaft further comprises a frame ground longitudinally positioned by the handle, the electroactive polymer actuator comprising an electroactive polymer sleeve at least partially encompassing the firing member and attached to the frame ground.

2. The surgical instrument of claim 1, wherein the electrical actuator further comprises:
   a locking plate of the electrical actuator having a through hole encompassing the firing member, the locking plate through hole sized for the locking plate to be in nonbinding contact with the firing member when the locking plate is in an unlocked state perpendicular to the firing member, and for the locking plate to be in binding contact with the firing member when the locking plate is in a locked state when tipped at an angle from perpendicular, the electrical actuator positioned to move the locking plate from a selected state to the other state of a group consisting of the unlocked state and the locked state.

3. The surgical instrument of claim 2, further comprising a resilient member biasing the locking plate to the locked state with distal motion of the firing member opposing the resilient member to move the locking plate to the unlocked state, the electrical actuator comprising an anti-backup cam tube position to selectively oppose and overcome the biasing of the resilient member.

4. The surgical instrument of claim 3, wherein the electroactive polymer actuators operatively configured to expand longitudinally when activated urging the anti-backup cam tube distally from the handle.

5. The surgical instrument of claim 3, further comprising:
   a proximally projecting yoke attached to the anti-backup cam tube;
   a manual release mechanism operatively configured to transmit a release motion to the proximally projecting yoke to manually actuate the anti-backup cam tube to release the locking plate.

6. The surgical instrument of claim 5, further comprising a manual release control operatively configured for user actuation, the manual release mechanism operatively configured to transmit the release motion from the manual release control.

7. The surgical instrument of claim 5, further comprising an unlocking feature coupled for motion in the handle to the firing member, an anti-backup release lever responsive to the unlocking feature moved to a distal position corresponding to full firing travel of the firing member to urge the proximally projecting yoke distally to unlock the locking plate.

8. The surgical instrument of claim 1, wherein the electrical actuator comprises a wound spring radially encompassing the firing member and an electrical device operatively configured to change an inner diameter of the wound spring between a selected one to the other of a group consisting of a locking state of a smaller diameter in binding contact with the firing member and an unlocking state of a larger diameter in non-binding contact with the firing member.

9. The surgical instrument of claim 8, wherein the wound spring further comprises a fixed end and a movable end the electroactive polymer actuator being position to move the movable end in a direction to effect the selected state, wherein the direction is one selected from the group consisting of linear movement and rotary movement.

10. The surgical instrument of claim 1, wherein the electroactive polymer sleeve is operatively configured to have an internal diameter for binding contact when in a selected one of an energized state and an unenergized state and a larger internal diameter for nonbinding contact when in the nonselected state.

11. The surgical instrument of claim 1, wherein the electroactive polymer sleeve when in an unenergized, relaxed state has an internal diameter larger than the firing member for nonbinding, unlocked contact and an energized state expanding a radial thickness of the electroactive polymer sleeve, wherein the shaft is operatively configured to constrain outward expansion of the electroactive polymer sleeve forcing the electroactive polymer sleeve into binding contact with the firing member when energized.

12. The surgical instrument of claim 1, wherein the end effector comprises a staple applying assembly.

13. The surgical instrument of claim 1, further comprising:
   the shaft comprising a frame ground attaching the end effector to the handle and the firing member guided for longitudinal reciprocating motion between the handle and the end effector;
   a firing trigger attached for movement to the handle;
   a multiple stroke firing mechanism in the handle operatively configured to distally advance the firing member incrementally with each firing stroke of the firing trigger;
   a retraction biasing urging the firing member to a retracted positioned; and the electrical actuator further comprising a means for electrically locking and unlocking the firing member for preventing inadvertent retraction of the firing member between firing strokes of the firing trigger.

14. The surgical instrument of claim 1, wherein the firing member comprises a firing rod.

15. The surgical instrument of claim 1, comprising:
the shaft comprising a frame ground attaching the end effector to the handle and the firing member guided for longitudinal reciprocating motion between the handle and the end effector;
a firing trigger attached for movement to the handle;
a multiple stroke firing mechanism in the handle operatively configured to distally advance the firing member incrementally with each firing stroke of the firing trigger;
a retraction biasing member positioned in the handle to assert a retraction bias on the firing member;
an anti-backup mechanism comprising the electrical actuator operatively configured to move between a locking and an unlocking state with the firing member; and
control circuitry operatively configured to activate the electrical actuator.

16. The surgical instrument of claim 15, wherein the anti-backup mechanism further comprises:
a locking plate having a through hole sized to disengage from the firing member when the locking plate is in a perpendicular position to the firing member, and locked to the firing member when the locking plate is in an angled position to the firing member;
a spring biasing the locking plate to a back tipped angled position;
a cam member opposing the spring; and
an electroactive polymer actuator positioned to move the cam member and the locking plate in turn to the locked state.

17. The surgical instrument of claim 15, further comprising a wound spring having a first end held against rotation by the shaft and a radially extended end, the electroactive polymer actuator of the electrical actuator being positioned to rotate the radially extended end to effect to change an inner diameter of the wound spring to effect a change of the state selected from a group consisting of the locked state and the unlocked state.

18. The surgical instrument of claim 15, wherein the elongate shaft further comprises a frame ground longitudinally positioned by the handle, the electroactive polymer actuator of the electrical actuator comprising an electroactive polymer sleeve encompassing the firing member and attached to the frame ground and operatively configured to have an internal diameter for binding contact when in a selected one of an energized state and an unenergized state and a larger internal diameter for nonbinding contact when in the nonselected state.

19. The surgical instrument of claim 18, wherein the electroactive polymer sleeve when in an unenergized, relaxed state has an internal diameter larger than the firing member for nonbinding, unlocked contact and an energized state expanding a radial thickness of the electroactive polymer sleeve, wherein the frame ground is operatively configured to constrain outward expansion of the electroactive polymer sleeve forcing the electroactive polymer sleeve into binding contact with the firing member when energized.

20. A surgical instrument, comprising:
an end effector;
a longitudinally reciprocating firing member distally coupled to the end effector;
a shaft having a distal end attached to the end effector and operatively configured to guide the firing member;
a handle attached to a proximal end of the shaft operatively configured to distally advance the firing member in a sequence of strokes; and
an electrical actuator physically grounded to the handle and responsive to an electrical signal to move between a non-binding and a binding position with the firing member to prevent longitudinal movement thereof, wherein the electrical actuator further comprises:
a locking plate of the electrical actuator having a through hole encompassing the firing member, the locking plate through hole sized for the locking plate to be in nonbinding contact with the firing member when the locking plate is in an unlocked state perpendicular to the firing member, and for the locking plate to be in binding contact with the firing member when the locking plate is in a locked state when tipped at an angle from perpendicular, the electrical actuator positioned to move the locking plate from a selected state to the other state of a group consisting of the unlocked state and the locked state.

* * * * *